United States Patent
Hüglin et al.

(10) Patent No.: US 6,184,375 B1
(45) Date of Patent: Feb. 6, 2001

(54) HYDROXYPHENYL TRIAZINES

(75) Inventors: Dietmar Hüglin, Freiburg (DE); Vien Van Toan, Rheinfelden (CH); Helmut Luther, Grenzach-Wyhlen (DE); Christophe Bulliard, Fribourg; Gerhard Rytz, Bern, both of (CH)

(73) Assignee: Ciba Specialty Chemicals Corporation, Tarrytown, NY (US)

( * ) Notice: Under 35 U.S.C. 154(b), the term of this patent shall be extended for 0 days.

(21) Appl. No.: 08/974,263

(22) Filed: Nov. 19, 1997

(30) Foreign Application Priority Data

Nov. 20, 1996 (CH) .................................... 2864/96

(51) Int. Cl.⁷ ........................ C07D 413/00; C07D 251/00
(52) U.S. Cl. .................................. 544/116; 544/216
(58) Field of Search ..................... 544/116, 216

(56) References Cited

U.S. PATENT DOCUMENTS

| | | |
|---|---|---|
| 3,113,940 | 12/1963 | Johns et al. . |
| 3,113,941 | 12/1963 | Johns et al. . |
| 3,113,942 | 12/1963 | Johns et al. . |
| 3,118,887 | 1/1964 | Hardy et al. . |
| 3,242,175 | 3/1966 | Duennenburger et al. . |
| 3,244,708 | 4/1966 | Duenenberger et al. . |
| 3,249,608 | 5/1966 | Biland et al. . |
| 4,619,956 | 10/1986 | Susi .............................. 524/87 |
| 4,826,978 | 5/1989 | Migdal et al. .............. 544/216 |
| 5,300,414 | 4/1994 | Leppard et al. . |
| 5,364,749 | 11/1994 | Leppard et al. . |
| 5,461,151 | 10/1995 | Waterman . |
| 5,489,503 | 2/1996 | Toan ............................. 544/113 |
| 5,538,840 | 7/1996 | Van Toan et al. . |
| 5,545,836 | 8/1996 | Reinehr et al. ............ 544/216 |
| 5,591,850 | 1/1997 | Birbaum et al. ........... 544/216 |
| 5,597,854 | 1/1997 | Birbaum et al. . |

FOREIGN PATENT DOCUMENTS

| | | |
|---|---|---|
| 0165608 | 12/1985 | (EP) . |
| 434608 | 6/1991 | (EP) . |
| 0497734 | 8/1992 | (EP) . |
| 0685223 | 12/1995 | (EP) . |
| 704437 | 4/1996 | (EP) . |
| 975966 | 11/1964 | (GB) . |
| 1321561 | 6/1973 | (GB) . |
| 2286774 | 8/1995 | (GB) . |
| 2294043 | 4/1996 | (GB) . |
| 1001381 | 10/1995 | (NL) . |
| 9405645 | 3/1994 | (WO) . |
| 94/18278 | 8/1994 | (WO) . |
| 9628431 | 9/1996 | (WO) . |
| 97/03643 | 2/1997 | (WO) . |
| 9703642 | 2/1997 | (WO) . |

OTHER PUBLICATIONS

Chemical Abstract 125:115934.
J. Phys. Chem. 1996, 100, pp. 14468–14475.
Chem. Abstr. 105:1241621k for EP 165608.
Derwent Abstr. 92–261146/32 for EP 497734.

*Primary Examiner*—Kriellion Sanders
(74) *Attorney, Agent, or Firm*—Luther A. R. Hall; Tyler A. Stevenson

(57) ABSTRACT

A description is given of compounds of the formula I

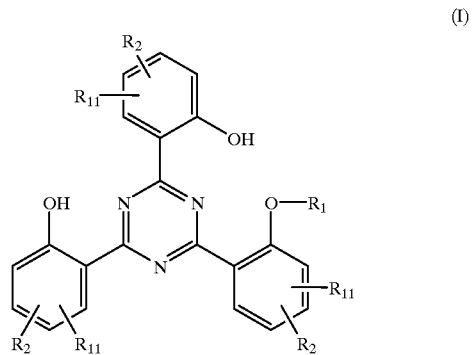

(I)

in which $R_1$ is $C_1$–$C_{18}$alkyl; $C_5$–$C_{12}$cycloalkyl; $C_3$–$C_6$alkenyl; phenyl; $C_1$–$C_{18}$alkyl which is substituted by phenyl, OH, $C_1$–$C_{18}$alkoxy, $C_5$–$C_{12}$cycloalkoxy, $C_3$–$C_{18}$alkenyloxy, halogen, —COOH, —COOR$_4$, —O—CO—R$_5$, —O—CO—O—R$_6$, —CO—NH$_2$, —CO—NHR$_7$, —CO—N(R$_7$)(R$_8$), CN, NH$_2$, NHR$_7$, —N(R$_7$)(R$_8$), —NH—CO—R$_5$, phenoxy, $C_1$–$C_{18}$alkyl-substituted phenoxy, phenyl-$C_1$–$C_4$alkoxy, $C_6$–$C_{15}$bicycloalkoxy, $C_6$–$C_{15}$bicycloalkylalkoxy, $C_6$–$C_{15}$bicycloalkenylalkoxy, or $C_6$–$C_{15}$tricycloalkoxy; $C_5$–$C_{12}$cycloalkyl which is substituted by OH, $C_1$–$C_4$alkyl, $C_2$–$C_6$alkenyl or —O—CO—R$_5$; glycidyl; —CO—R$_9$ or —SO$_2$—R$_{10}$; or $R_1$ is $C_3$–$C_{50}$alkyl which is interrupted by one or more oxygen atoms and/or substituted by OH, phenoxy or $C_7$–$C_{18}$alkylphenoxy;

or $R_1$ denotes the specific polymerizable radicals indicated in claim 1;

$R_2$ is $C_6$–$C_{18}$alkyl; $C_2$–$C_6$alkenyl; phenyl; $C_7$–$C_{11}$phenylalkyl; COOR$_4$; CN; NH—CO—R$_5$; halogen; trifluoromethyl; —O—R$_3$;

$R_3$ embraces the definitions given for $R_1$;

the radicals $R_{11}$ independently of one another are H; $C_1$–$C_{18}$alkyl; $C_3$–$C_6$alkenyl; phenyl; $C_7$–$C_{11}$phenylalkyl; halogen or $C_1$–$C_{18}$alkoxy, and the remaining radicals embrace the definitions given in claim 1, at least one of the radicals $R_1$, $R_2$ and $R_{11}$ containing 4 or more carbon atoms. The novel compounds are effective as stabilizers for organic material against the damaging effect of light, oxygen and heat; they are also suitable for use in skin or hair protection preparations.

7 Claims, No Drawings

HYDROXYPHENYL TRIAZINES

The invention relates to novel compounds of the hydroxyphenyl-s-triazine type containing one blocked and 2 free o-hydroxyl groups, to the use of these compounds for stabilizing organic material, especially in plastics, coating materials, cosmetic preparations, sun screen lotions or photographic material, against damage by light, oxygen and/or heat, and to correspondingly stabilized organic material.

When it is desired to increase the stability of an organic material, especially a coating, to light, it is common to add a light stabilizer. One very frequently employed class of light stabilizers are the UV absorbers, which protect the material by absorbing the harmful radiation via chromophores. One important group of UV absorbers are the triphenyl-s-triazines, as are described, inter alia, in the publications U.S. Pat. No. 3,118,887, U.S. Pat. No. 3,242,175, U.S. Pat. No. 3,244,708, GB-A-1 321 561, EP-A-0 434 608, U.S. Pat. No. 4,619,956, U.S. Pat. No. 5,364,749, U.S. Pat. No. 5,461,151, EP-A-0 704 437 and WO-96/28431.

Also known are individual compounds of the hydroxyphenyl-s-triazine type some or all of whose hydroxyl groups in ortho position are blocked (U.S. Pat. No. 3,113,940, U.S. Pat. No. 3,113,941, U.S. Pat. No. 3,113,942, GB-A-975 966, U.S. Pat. No. 3,249,608: U.S. Pat. No. 5,597,854, WO-94/05645).

Specific compounds from the class of the trisaryl-s-triazines have now been found which, surprisingly, possess particularly good stabilizer properties. The invention therefore provides a compound of the formula I

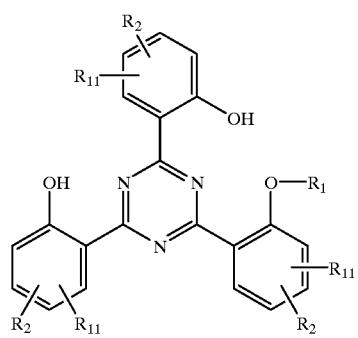

in which
$R_1$ is $C_1$–$C_{18}$alkyl; $C_5$–$C_{12}$cycloalkyl; $C_3$–$C_{18}$alkenyl; phenyl; $C_1$–$C_{18}$alkyl which is substituted by phenyl, OH, $C_1$–$C_{18}$alkoxy, $C_5$–$C_{12}$cycloalkoxy, $C_3$–$C_{18}$alkenyloxy, halogen, —COOH, —COOR$_4$, —O—CO—R$_5$, —O—CO—O—R$_6$, —CO—NH$_2$, —CO—NHR$_7$, —CO—N(R$_7$)(R$_8$), CN, NH$_2$, NHR$_7$, —N(R$_7$)(R$_8$), —NH—CO—R$_5$, phenoxy, $C_1$–$C_{18}$alkyl-substituted phenoxy, phenyl-$C_1$–$C_4$alkoxy, $C_6$–$C_{15}$bicycloalkoxy, $C_6$–$C_{15}$bicycloalkylalkoxy, $C_6$–$C_{15}$bicycloalkenylalkoxy, or $C_6$–$C_{15}$tricycloalkoxy; $C_5$–$C_{12}$cycloalkyl which is substituted by OH, $C_1$–$C_4$alkyl, $C_2$–$C_6$alkenyl or —O—CO—R$_5$; —CO—R$_9$ or —SO$_2$—R$_{10}$; or R$_1$ is $C_3$–$C_{50}$alkyl which is interrupted by one or more oxygen atoms and/or substituted by OH, phenoxy or $C_7$–$C_{18}$alkylphenoxy;

or $R_1$ is one of the definitions —A; —CH$_2$—CH(XA)—CH$_2$—O—R$_{12}$; —CR$_{13}$R'$_{13}$—(CH$_2$)$_m$—X—A; —CH$_2$—CH(OA)—R$_{14}$; —CH$_2$—CH(OH)—CH$_2$—XA;

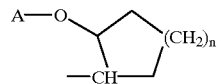

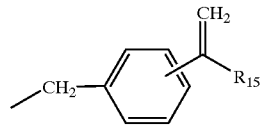

—CR$_{15}$R'$_{15}$—C(=CH$_2$)—R"$_{15}$; —CR$_{13}$R'$_{13}$—(CH$_2$)$_m$—CO—X—A;
—CR$_{13}$R'$_{13}$—(CH$_2$)$_m$—CO—O—CR$_{15}$R'$_{15}$—C(=CH$_2$)—R"$_{15}$ or —CO—O—CR$_{15}$R'$_{15}$—C(=CH$_2$)—R"$_{15}$, where A is —CO—CR$_{16}$=CH—R$_{17}$; the radicals $R_2$, independently of one another, are $C_6$–$C_{18}$alkyl; $C_2$–$C_6$alkenyl; phenyl; $C_7$–$C_{11}$phenylalkyl; COOR$_4$; CN; NH—CO—R$_5$; halogen; trifluoromethyl; —O—R$_3$;

$R_3$ embraces the definitions given for $R_1$;

$R_4$ is $C_1$–$C_{18}$alkyl; $C_3$–$C_{18}$alkenyl; phenyl; $C_7$–$C_{11}$phenylalkyl; $C_5$–$C_{12}$cycloalkyl; or is $C_3$–$C_{50}$alkyl, which is interrupted by one or more —O—, —NH—, —NR$_7$—, —S— and can be substituted by OH, phenoxy or $C_7$–$C_{18}$alkylphenoxy;

$R_5$ is H; $C_1$–$C_{18}$alkyl; $C_2$–$C_{18}$alkenyl; $C_5$–$C_{12}$cycloalkyl; phenyl; $C_7$–$C_{11}$phenylalkyl $C_6$–$C_{15}$bicycloalkyl; $C_6$–$C_{15}$bicycloalkenyl; $C_6$–$C_{15}$tricycloalkyl;

$R_6$ is H; $C_1$–$C_{18}$alkyl; $C_3$–$C_{18}$alkenyl; phenyl; $C_7$–$C_{11}$phenylalkyl; $C_5$–$C_{12}$cycloalkyl $R_7$ and $R_8$, independently of one another are $C_1$–$C_{12}$alkyl; $C_3$–$C_{12}$alkoxyalkyl; $C_4$–$C_{16}$dialkylaminoalkyl; or are $C_5$–$C_{12}$cycloalkyl; or together are $C_3$–$C_9$alkylene, $C_3$–$C_9$oxaalkylene or $C_3$–$C_9$azaalkylene;

$R_9$ is $C_1$–$C_{18}$alkyl; $C_2$–$C_{18}$alkenyl; phenyl; $C_5$–$C_{12}$cycloalkyl; $C_7$–$C_{11}$phenylalkyl; $C_6$–$C_{15}$bicycloalkyl, $C_6$–$C_{15}$bicycloalkylalkyl, $C_6$–$C_{15}$bicycloalkenyl, or $C_6$–$C_{15}$tricycloalkyl;

$R_{10}$ is $C_1$–$C_{12}$alkyl; phenyl; naphthyl or $C_7$–$C_{14}$alkylphenyl;

the radicals $R_{11}$ independently of one another are H; $C_1$–$C_{18}$alkyl; $C_3$–$C_6$alkenyl; phenyl; $C_7$–$C_{11}$phenylalkyl; halogen; $C_1$–$C_{18}$alkoxy;

$R_{12}$ is $C_1$–$C_{18}$alkyl; $C_3$–$C_{18}$alkenyl; phenyl; phenyl which is substituted by one to three radicals $C_1$–$C_8$alkyl, $C_1$–$C_8$alkoxy, $C_3$–$C_8$alkenoxy, halogen or trifluoromethyl;

or is $C_7$–$C_{11}$phenylalkyl; $C_5$–$C_{12}$cycloalkyl; $C_6$–$C_{15}$tricycloalkyl; $C_6$–$C_{15}$bicycloalkyl; $C_6$–$C_{15}$bicycloalkylalkyl; $C_6$–$C_{15}$bicycloalkenylalkyl; —CO—R$_5$; or is $C_3$–$C_{50}$alkyl which is interrupted by one or more —O—, —NH—, —NR$_7$—, —S— and can be substituted by OH, phenoxy or $C_7$–$C_{18}$alkylphenoxy;

$R_{13}$ and R'$_{13}$ independently of one another are H; $C_1$–$C_{18}$alkyl; phenyl;

$R_{14}$ is $C_1$–$C_{18}$alkyl; $C_3$–$C_{12}$alkoxyalkyl; phenyl; phenyl-$C_1$–$C_4$alkyl;

$R_{15}$, R'$_{15}$ and R"$_{15}$ independently of one another are H or CH$_3$;

$R_{16}$ is H; —$CH_2$—COO—$R_4$; $C_1$–$C_4$alkyl; or CN;
$R_{17}$ is H; —COO$R_4$; $C_1$–$C_{17}$alkyl; or phenyl;
X is —NH—; —N$R_7$—; —O—; —NH—$(CH_2)_p$—NH—; or —O—$(CH_2)_q$—NH—;
and the indices
m is a number 0–19;
n is a number 1–8;
p is a number 0–4; and
q is a number 2–4;
where at least one of the radicals $R_1$, $R_2$ and $R_{11}$ in formula I contains 2 or more carbon atoms.

Preferably, at least one of the radicals $R_1$, $R_2$, $R_{11}$ in formula I and in formula II below contains 3 or more carbon atoms, especially 4 or more carbon atoms.

Within the scope of the stated definitions the radicals $R_1$ to $R_{10}$, $R_{12}$ to $R_{14}$, $R_{16}$ and $R_{17}$ as alkyl are branched or unbranched alkyl, for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylun-decyl, dodecyl, 1,1,3,3,5,5-hexamethylhexyl, tridecyl, tetradecyl, pentadecyl, hexadecyl, heptadecyl, octadecyl.

The radicals $R_1$, $R_3$ to $R_9$ and $R_{12}$ as $C_5$–$C_{12}$cycloalkyl comprise cyclopentyl, cyclohexyl, cycloheptyl, cyclooctyl, cyclononyl, cyclodecyl, cycloundecyl, cyclododecyl. Preference is given to cyclopentyl, cyclohexyl, cyclooctyl and cyclododecyl.

Within the scope of the stated definitions, $R_1$ to $R_6$, $R_9$, $R_{11}$, and $R_{12}$ as alkenyl embrace, inter alia, allyl, isopropenyl, 2-butenyl, 3-butenyl, isobutenyl, n-penta-2,4-dienyl, 3-methylbut-2-enyl, n-oct-2-enyl, n-dodec-2-enyl, isododecenyl, n-dodec-2-enyl or n-octadec-4-enyl.

Substituted alkyl, cycloalkyl or phenyl radicals can be substituted one or more times and can carry substituents on the bonding carbon atom (in α-position) or on other carbon atoms; if the substituent bonds by means of a heteroatom (for example alkoxy) it is preferably not in α-position and the substituted alkyl radical contains 2, especially 3, or more carbon atoms. Two or more substituents bond preferably to different carbon atoms.

Alkyl interrupted by —O—, —NH—, —N$R_7$—, —S— can be interrupted by one or more of these groups, one group in each case being inserted, in general into one bond, and hetero-hetero bonds, for example O—O, S—S, NH—NH, etc., not occurring; if the interrupted alkyl is additionally substituted, the substituents are generally not α to the heteroatom. If two or more interrupting groups of the type —O—, —NH—, —N$R_7$—, —S— occur in one radical, they are usually identical.

Aryl is generally an aromatic hydrocarbon radical, for example phenyl, biphenylyl or naphthyl, preferably phenyl and biphenylyl. Aralkyl is generally alkyl substituted by aryl, especially by phenyl; thus $C_7$–$C_{20}$aralkyl comprises, for example, benzyl, α-methylbenzyl, phenylethyl, phenylpropyl, phenylbutyl, phenylpentyl and phenylhexyl; $C_7$–$C_{11}$phenylalkyl preferably embraces benzyl, α-methylbenzyl and α,α-dimethylbenzyl.

Alkylphenyl and alkylphenoxy are alkyl-substituted phenyl and phenoxy, respectively.

A halogen substituent is —F, —Cl, —Br or —I; preference is given to —F or —Cl, especially —Cl.

$C_1$–$C_{20}$alkylene is, for example, methylene, ethylene, propylene, butylene, pentylene, hexylene, etc. The alkyl chain here can also be branched, as in isopropylene, for example.

$C_4$–$C_{12}$cycloalkenyl is, for example 2-cyclobuten-1-yl, 2-cyclopenten-1-yl, 2,4-cyclopentadien-1-yl-, 2-cyclohexen-1-yl, 2-cyclohepten-1-yl or 2-cycloocten-1-yl.

$C_6$–$C_{15}$bicycloalkyl is, for example, bornyl, norbornyl, [2.2.2]bicyclooctyl. Preference is given to bornyl and norbornyl, especially bornyl and norborn-2-yl.

$C_6$–$C_{15}$bicycloalkoxy is, for example, bornyloxy or norborn-2-yloxy.

$C_6$–$C_{15}$bicycloalkyl-alkyl or -alkoxy is bicycloalkyl-substituted alkyl or alkoxy, the total number of carbon atoms being 6–15; examples are norbornane-2-methyl and norbornyl-2-methoxy.

$C_6$–$C_{15}$bicycloalkenyl is, for example, norbornenyl, norbornadienyl. Preference is given to norbornenyl, especially norborn-5-ene.

$C_6$–$C_{15}$bicycloalkenylalkoxy is bicycloalkenyl-substituted alkoxy, the total number of carbon atoms being 6–15; one example is norborn-5-ene-2-methoxy.

$C_6$–$C_{15}$tricycloalkyl is, for example, 1-adamantyl, 2-adamantyl. Preference is given to 1-adamantyl.

$C_6$–$C_{15}$tricycloalkoxy is, for example, adamantyloxy.

$C_3$–$C_{12}$heteroaryl is, preferably, pyridinyl, pyrimidinyl, triazinyl, pyrrolyl, furanyl, thiophenyl or quinolinyl.

Typical compounds of the formula I comprise those in which $R_1$ is $C_1$–$C_{18}$alkyl; $C_5$–$C_{12}$cycloalkyl; $C_3$–$C_{12}$alkenyl; phenyl; $C_1$–$C_{18}$alkyl which is substituted by phenyl, OH, $C_{1-18}$alkoxy, $C_5$–$C_{12}$cycloalkoxy, $C_3$–$C_{18}$alkenyloxy, halogen, —COOH, —COO$R_4$, —O—CO—$R_5$, —O—CO—O—$R_6$, —CO—$NH_2$, —CO—NH$R_7$, —CO—N($R_7$)($R_8$), CN, $NH_2$, NH$R_7$, —N($R_7$)($R_8$), —NH—CO—$R_5$, phenoxy, $C_1$–$C_{18}$alkyl-substituted phenoxy, phenyl-$C_1$–$C_4$alkoxy, bornyloxy, norborn-2-yloxy, norbornyl-2-methoxy, norborn-5-ene-2-methoxy, adamantyloxy; $C_5$–$C_{12}$cycloalkyl which is substituted by OH, $C_1$–$C_4$alkyl, $C_2$–$C_6$alkenyl and/or —O—CO—$R_5$; glycidyl; —CO—$R_9$ or —$SO_2$—$R_{10}$; or $R_1$ is $C_3$–$C_{50}$alkyl which is interrupted by one or more oxygen atoms and/or is substituted by OH, phenoxy or $C_7$–$C_{18}$alkylphenoxy;

or $R_1$ is one of the definitions —A; —$CH_2$—CH(XA)—$CH_2$—O—$R_{12}$; —$CR_{13}R'_{13}$—$(CH_2)_m$—X—A; —$CH_2$—CH(OA)—$R_{14}$; —$CH_2$—CH(OH)—$CH_2$—XA;

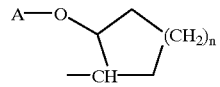

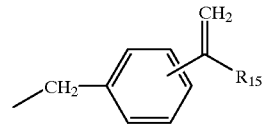

—$CR_{15}R'_{15}$—C(=$CH_2$)—R"$_{15}$; —$CR_{13}R'_{13}$—$(CH_2)_m$—CO—X—A;
—$CR_{13}R'_{13}$—$(CH_2)_m$—CO—O—$CR_{15}R'_{15}$—C(=CH)—R"$_{15}$ or —CO—O—$CR_{15}R'_{15}$—C(=$CH_2$)—R"$_{15}$, where A is —CO—$CR_{16}$=CH—$R_{17}$; the radicals $R_2$ are $C_6$–$C_{18}$alkyl; $C_2$–$C_6$alkenyl; phenyl; —O—$R_3$ or —NH—CO—$R_5$ and the radicals $R_3$ independently of one another embrace the definitions given for $R_1$;

$R_4$ is $C_1$–$C_{18}$alkyl; $C_3$–$C_{18}$alkenyl; phenyl; $C_7$–$C_{11}$phenylalkyl; $C_5$–$C_{12}$cycloalkyl; or is $C_3$–$C_{50}$alkyl, which is interupted by one or more —O—, —NH—, —NR$_7$—, —S— and can be substituted by OH, phenoxy or $C_7$–$C_{18}$alkylphenoxy;

$R_5$ is H; $C_1$–$C_{18}$alkyl; $C_2$–$C_{18}$alkenyl; $C_5$–$C_{12}$cycloalkyl; phenyl; $C_7$–$C_{11}$phenylalkyl; norborn-2-yl; norborn-5-en-2-yl; adamantyl;

$R_6$ is H; $C_1$–$C_{18}$alkyl; $C_3$–$C_{18}$alkenyl; phenyl; $C_7$–$C_{11}$phenylalkyl; $C_5$–$C_{12}$cycloalkyl;

$R_7$ and $R_8$ independently of one another are $C_1$–$C_{12}$alkyl; $C_3$–$C_{12}$alkoxyalkyl; $C_4$–$C_{16}$dialkylaminoalkyl; or are $C_5$–$C_{12}$cycloalkyl; or together are $C_3$–$C_9$alkylene, $C_3$–$C_9$oxaalkylene or $C_3$–$C_9$azaalkylene; $R_9$ is $C_1$–$C_{18}$alkyl; $C_2$–$C_{18}$alkenyl; phenyl; $C_5$–$C_{12}$cycloalkyl; $C_7$–$C_{11}$phenylalkyl; norborn-2-yl; norborn-5-en-2-yl; adamantyl;

$R_{10}$ is $C_1$–$C_{12}$alkyl; phenyl; naphthyl or $C_7$–$C_{14}$alkylphenyl; the radicals $R_{11}$ independently of one another are H; $C_1$–$C_{18}$alkyl; or $C_7$–$C_{11}$phenylalkyl;

$R_{12}$ is $C_1$–$C_{18}$alkyl; $C_3$–$C_{18}$alkenyl; phenyl; phenyl which is substituted by one to three $C_1$–$C_8$alkyl, $C_1$–$C_8$alkoxy, $C_3$–$C_8$alkenoxy, halogen or trifluoromethyl; or is $C_7$–$C_{11}$phenylalkyl; $C_5$–$C_{12}$cycloalkyl; 1-adamantyl; 2-adamantyl; norbornyl; norbornane-2-methyl-; —CO—R$_5$; or is $C_3$–$C_{50}$alkyl which is interrupted by one or more —O—, —NH—, —NR$_7$—, —S— and can be substituted by OH, phenoxy or $C_7$–$C_{18}$alkylphenoxy;

$R_{13}$ and $R'_{13}$ independently of one another are H; $C_1$–$C_{18}$alkyl; phenyl;

$R_{14}$ is $C_1$–$C_{18}$alkyl; $C_3$–$C_{12}$alkoxyalkyl; phenyl-$C_1$–$C_4$alkyl;

$R_{15}$, $R'_{15}$ and $R''_{15}$ independently of one another are H or CH$_3$;

$R_{16}$ is H; —CH$_2$—COO—R$_4$; $C_1$–$C_4$alkyl; or CN;

$R_{17}$ is H; —COOR$_4$; $C_1$–$C_{17}$alkyl; or phenyl;

X is —NH—; —NR$_7$—; —O—; —NH—(CH$_2$)$_p$—NH—; or —O—(CH$_2$)$_q$—NH—;

and the indices m is a number 0–19;

n is a number 1–8;

p is a number 0–4; and q is a number 2–4;

especially those of the formula II

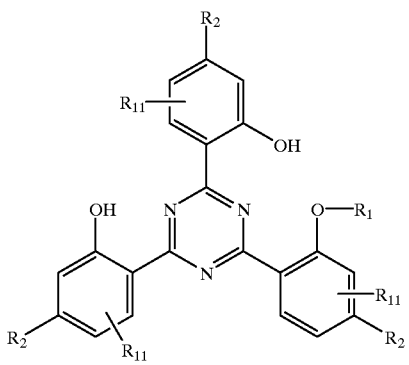

(II)

in which $R_1$, $R_2$ and $R_{11}$ are as defined above.

Among the compounds of the formula II preference is given to those in which the radicals $R_2$ are identical, especially to those in which the radicals $R_2$ have the definition —O—$R_3$, and in particular to those in which $R_{11}$ is H.

Compounds of the formulae I or II comprising a polymerizable double bond, and —of these—especially those in which $R_1$ and/or $R_3$ are/is a radical —A; —CH$_2$—CH(XA)—CH$_2$—O—R$_{12}$; —CR$_{13}$R'$_{13}$—(CH$_2$)$_m$—X—A; —CH$_2$—CH(OA)—R$_{14}$; —CH$_2$—CH(OH)—CH$_2$—XA;

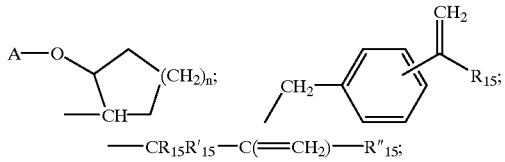

—CR$_{15}$R'$_{15}$—C(=CH$_2$)—R''$_{15}$;

—CR$_{15}$R'$_{15}$((=CH$_2$)... —CR$_{13}$R'$_{13}$—(CH$_2$)$_m$—CO—X—A; —CR$_{13}$R'$_{13}$—(CH$_2$)$_m$—CO—O—CR$_{15}$R'$_{15}$—C(=CH$_2$)—R''$_{15}$ or —CO—O—CR$_{15}$R'$_{15}$—C(=CH$_2$)—R''$_{15}$ or $C_5$–$C_{12}$cycloalkyl which is substituted by $C_2$–$C_6$alkenyl, by OH and $C_2$–$C_6$alkenyl, or by —O—CO—R$_5$, where R$_5$ is $C_2$–$C_3$alkenyl and A is —CO—CR$_{16}$=CH—R$_{17}$, constitute a subject of special interest.

In particularly preferred compounds, X is —O—. Preferably, in such compounds, $R_{12}$ is $C_1$–$C_{18}$alkyl or $C_5$–$C_{12}$cycloalkyl; $R_{13}$ is H or $C_1$–$C_{18}$alkyl; R'$_{13}$ is H; $R_{16}$ is H or methyl; $R_{17}$ is H.

Preference is given to compounds of the formula II in which $R_1$ is $C_1$–$C_{18}$alkyl; $C_5$–$C_{12}$cycloalkyl; phenyl; $C_1$–$C_{18}$alkyl which is substituted by phenyl, OH, $C_1$–$C_{18}$alkoxy, $C_5$–$C_{12}$cycloalkoxy, —COOH, —COOR$_4$, —O—CO—R$_5$, phenyl-$C_1$–$C_4$alkoxy; or is cyclohexyl which is substituted by OH, $C_1$–$C_4$alkyl, $C_2$–$C_6$alkenyl and/or —O—CO—R$_5$;

or $R_1$ is one of the definitions —A; —CH$_2$—CH(XA)—CH$_2$—O—R$_{12}$; —CR$_{13}$R'$_{13}$—(CH$_2$)$_m$—X—A; —CH$_2$—CH(OA)—R$_{14}$; —CH$_2$—CH(OH)—CH$_2$—XA;

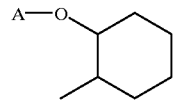

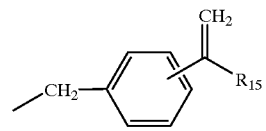

—CR$_{15}$R'$_{15}$—C(=CH$_2$)—R''$_{15}$; —CR$_{13}$R'$_{13}$—(CH$_2$)$_m$—CO—X—A;

Glycidyl; —CR$_{13}$R'$_{13}$—(CH$_2$)$_m$—CO—O—CR$_{15}$R'$_{15}$—C(=CH$_2$)—R''$_{15}$ or —CO—O—CR$_{15}$R'$_{15}$—C(=CH$_2$)—R''$_{15}$, where A is —CO—CR$_{16}$=CH—R$_{17}$; the radicals $R_2$ are —O—R$_3$ or —NH—CO—R$_5$ and the radicals $R_3$ independently of one another embrace the definitions given for $R_1$;

$R_4$ is $C_1$–$C_{18}$alkyl; $C_7$–$C_{11}$phenylalkyl; cyclohexyl; or $C_3$–$C_{50}$alkyl which is interrupted by —O— and can be substituted by OH, phenoxy or $C_7$–$C_{18}$alkylphenoxy;

$R_5$ is $C_1$–$C_{18}$alkyl; cyclohexyl; phenyl; $C_7$–$C_{11}$phenylalkyl;

$R_7$ is $C_1$–$C_{12}$alkyl or cyclohexyl;

$R_{11}$, is H;

$R_{12}$ is $C_1$–$C_{18}$alkyl; phenyl; $C_1$–$C_8$alkyl- or $C_1$–$C_8$alkoxy-substituted phenyl; $C_7$–$C_{11}$ phenylalkyl $C_5$–$C_{12}$cycloalkyl; —CO—$R_5$; or is $C_3$–$C_{50}$alkyl which is interrupted by —O— and can be substituted by OH, phenoxy or $C_7$–$C_{18}$alkylphenoxy;

$R_{13}$ is H; $C_1$–$C_{18}$alkyl; phenyl;

$R'_{13}$ is H;

$R_{14}$ is $C_1$–$C_{18}$alkyl; phenyl; phenyl-$C_1$–$C_4$alkyl;

$R_{15}$, $R'_{15}$ and $R''_{15}$ independently of one another are H or $CH_3$;

$R_{16}$ is H; —$CH_2$—COO—$R_4$; $C_1$–$C_4$alkyl; or CN;

$R_{17}$ is H; —COOR$_4$; $C_1$–$C_{17}$alkyl; or phenyl;

X is —NH—; —NR$_7$—; or —O—;

and m is a number 0–19.

Particularly preferred compounds of the formula II are those in which $R_1$ is $C_1$–$C_{18}$alkyl; $C_5$–$C_{12}$cycloalkyl; $C_1$–$C_{18}$alkyl which is substituted by phenyl, OH, $C_1$–$C_{18}$alkoxy, —COOR$_4$, —O—CO—R$_5$; or cyclohexyl which is substituted by OH, $C_1$–$C_4$alkyl, $C_2$–$C_6$alkenyl; or $R_1$ is one of the definitions —A; —$CH_2$—CH(XA)—$CH_2$—O—$R_{12}$; —$CR_{13}R'_{13}$—(CH$_2$)$_m$—X—A; —$CH_2$—CH(OA)—$R_{14}$; —$CH_2$—CH(OH)—$CH_2$—XA;

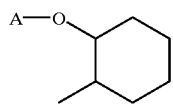

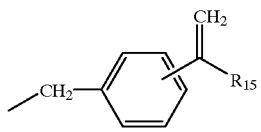

—$CR_{15}R'_{15}$—C(=$CH_2$)—$R''_{15}$; —$CR_{13}R'_{13}$—(CH$_2$)$_m$—CO—X—A; —$CR_{13}R'_{13}$—(CH$_2$)$_m$—CO—O—$CR_{15}R'_{15}$—C(=$CH_2$)—$R''_{15}$ or —CO—O—$CR_{15}R'_{15}$—C(=$CH_2$)—$R''_{15}$ where A is —CO—$CR_{16}$=CH—$R_{17}$; the radicals $R_2$ are —O—$R_3$ or —NH—CO—$R_5$ and the radicals $R_3$ independently of one another embrace the definitions given for $R_1$;

$R_4$ is $C_1$–$C_{18}$alkyl; $C_7$–$C_{11}$phenylalkyl or cyclohexyl;

$R_5$ is $C_1$–$C_{18}$alkyl;

$R_{11}$ is H;

$R_{12}$ is $C_1$–$C_{18}$alkyl; $C_7$–$C_{11}$phenylalkyl; $C_5$–$C_{12}$cycloalkyl; —CO—$R_5$;

$R_{13}$ is H or $C_1$–$C_{18}$alkyl;

$R'_{13}$ is H;

$R_{14}$ is $C_1$–$C_{18}$alkyl;

$R_{15}$, $R'_{15}$, $R''_{15}$, $R_{16}$ and $R_{17}$ independently of one another are H or $CH_3$;

X is —O—;

and m is a number 0–19.

Of especial interest are compounds of the formula II in which $R_2$ is —OR$_3$, $R_1$ and $R_3$ independently of one another are $C_1$–$C_{18}$alkyl; or are $C_2$–$C_6$alkyl which is substituted by OH, $C_1$–$C_{18}$alkoxy and/or —COOR$_4$; or are $CH_2COOR_4$; or are cyclohexyl which is unsubstituted or substituted by OH and/or $C_2$–$C_3$alkenyl; and $R_4$ is $C_1$–$C_6$alkyl; and $R_{11}$ is hydrogen.

Of particular technical interest are those compounds of the formula II in which $R_2$ is —OR$_3$, $R_1$ and $R_3$ independently of one another are $C_1$–$C_{18}$alkyl, especially branched $C_5$–$C_{18}$alkyl; and $R_{11}$, is hydrogen. These compounds are particularly suitable for use as UV filters in cosmetic, pharmaceutical and veterinary preparations.

To prepare compounds of the formula I and especially of the formula II it is judicious to start from compounds of the formula A and, respectively, of the formula A',

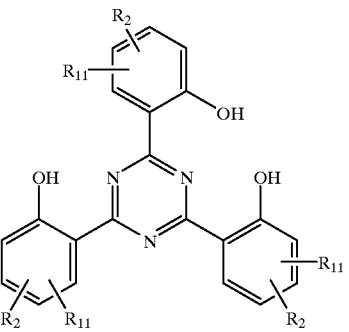

(A)

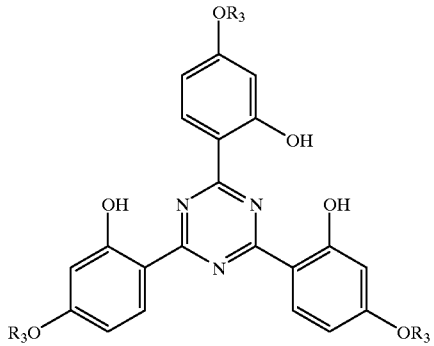

(A')

in which the radicals $R_2$ independently of one another are $C_6$–$C_{18}$alkyl; $C_2$–$C_6$alkenyl; phenyl; $C_7$–$C_{11}$phenylalkyl; COOH; COOR$_4$; CN; NH—CO—$R_5$; halogen; trifluoromethyl; or —OR$_3$; and $R_3$, $R_4$, $R_5$ and $R_{11}$, have the definitions given for formula I, $R_3$ additionally embracing H.

Compounds of the formulae A and A' are known or can be obtained in analogy to known compounds by common methods, for example in accordance with or in analogy to one of the methods given in EP-A-434 608 or in the publication by H. Brunetti and C. E. Lühi, Helv. Chim. Acta 55, 1566 (1972), by Friedel-Crafts addition of halotriazines onto corresponding phenols. This can be followed by a further reaction in accordance with known methods, for example for esterifying free carboxyl groups to give esters in which $R_2$ is COOR$_4$.

Further details on starting compounds which can be used and on their preparation can be found in the literature cited at the outset and in EP-A-165 608.

Other methods of preparing starting compounds of the formula A are described by Cousin and Volmar, Bull. Soc. Chim. Fr. 15, 414–421 (1914), U.S. Pat. No. 3,113,942 or EP-A-648753; in accordance with or in analogy to these methods it is possible to trimerize 3 equivalents of a 2-hydroxybenzonitrile of the formula B

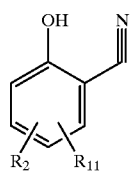

(B)

or of a 2-hydroxybenzamide of the formula C

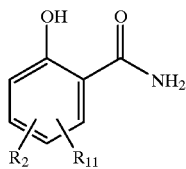

(C)

at elevated temperature, usually in the range 180–260° C., to give the compound of the formula A. This route is particularly suitable for compounds of the formula A in which $R_2$ is not OH or $OR_3$.

A particularly preferred starting compound of the formula A is tris(2,4-dihydroxyphenyl)-1,3,5-triazine; the novel compounds obtainable therefrom by preparation methods indicated below correspond to the formula II in which $R_2$ is —$OR_3$ and $R_{11}$ is hydrogen.

Options for the further reaction of the compound of the formula A to the compound of the formula I, and especially of the formula II, include the following:

a) Stepwise Reaction of Free OH Groups with Halides or Sulfates

This is done using, for each OH to be reacted, about one equivalent of a reagent $R_1$-Hal in which Hal is a halogen atom, preferably Cl, and $R_1$ embraces the definitions given in connection with formula I above, together with about one equivalent of base. $R_1$-Hal can also be a mixture of reagents. Instead of the halide $R_1$-Hal it is also posisble to use one equivalent of a sulfate (½ $R_1$—O—$SO_2$—O—$R_1$). If the intention is to introduce not only the radical —$R_1$ but also another, different radical ($R_2$ in the definition of —$OR_3$) then it is judicious first of all to carry out reaction with the required number of equivalents of $R_3$-Hal, where $R_3$ embraces the definitions given for $R_1$, and base and then reaction with one equivalent of $R_1$-Hal.

The reaction is preferably carried out in an organic solvent, for example an aromatic or aliphatic hydrocarbon, alcohol, ether, ester or amide of appropriate boiling range; preferred solvents are toluene, xylene, propanol, butanol, 2-methoxyethanol, 2-ethoxyethanol, diethylene glycol dimethyl ether (diglyme), dimethylformamide (DMF), dimethyl sulfoxide (DMSO). Suitable bases are organic or, preferably, inorganic bases such as hydroxides, oxides or carbonates; important examples are alkali metal hydroxides and carbonates, such as KOH, NaOH, $K_2CO_3$, $Na_2CO_3$. The reaction temperature is usually in the range 80–180° C., preferably in the range 100–150° C. The reaction can also be carried out as a 2-phase reaction in the presence of phase transfer catalysts such as tetraalkylammonium salts, for example; in this case the halide or sulfate is usually— and especially when it is employed as a pure alkylating reagent—present in the organic phase and the triazine precursor in the aqueous phase.

For instance, a compound of the formula II, in which $R_2$ is —$OR_3$ can be obtained, for example, by the following reaction schemes:

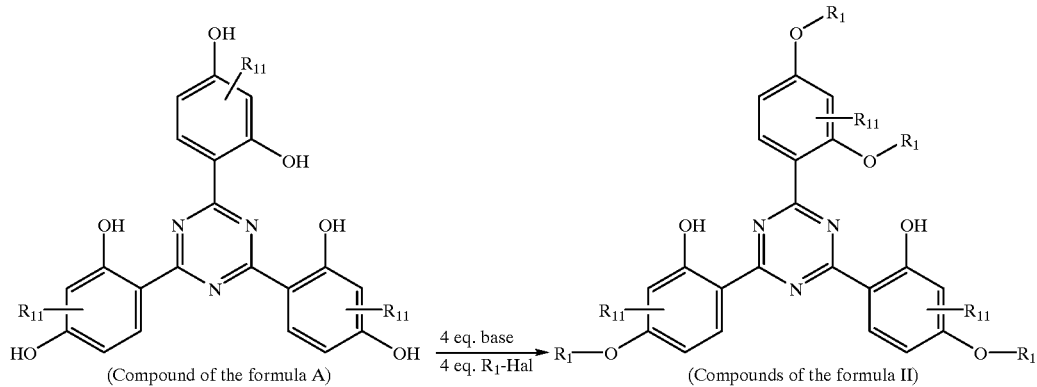

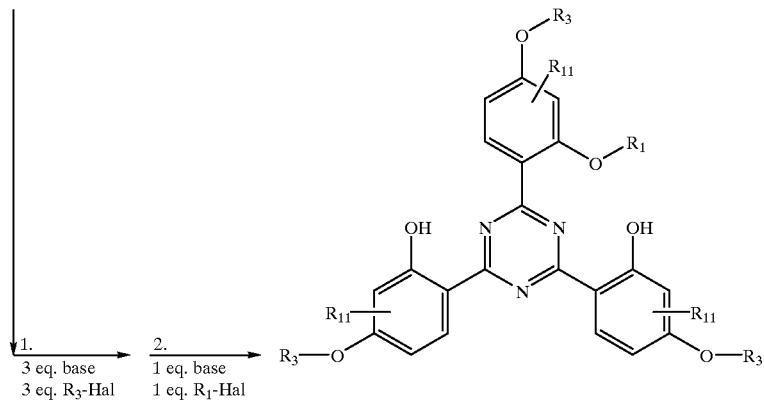

b) Stepwise Reaction of Free OH Groups with Epoxides

Instead of the reagents described under a) it is also possible to employ epoxides. For each OH group to be reacted, in each case about 1 equivalent or more of an epoxide of the type

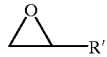

is employed, together with a catalyst, in bulk or in a solvent. This reaction usually takes place without the addition of bases. The primary reaction product of the formula I or II, in which $R_3$ or, if appropriate $R_3$ and $R_1$ correspond to the formula —$CH_2$—CH(OH)—R' can, if desired, be reacted further by known methods, for example with etherification or esterification of the aliphatic OH group.

If the intention is to introduce not only the radical —$R_3$ as —$CH_2$—CH(OH)—R' but also another, different radical $R_1$, then it is judicious first of all to carry out reaction with the required number of equivalents of

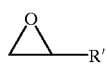

, where usually no excess is used and where —$CH_2$—CH(OH)—R' embraces the definitions given for $R_1$, and then to carry out reaction with one equivalent of the desired further reagent, for example $R_1$-Hal and base, or with one further equivalent of

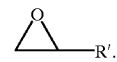

Conversely, in accordance with a) it is also possible first to introduce a radical —$R_3$ and then to react the reaction product with

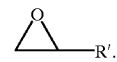

to give the compound of the formula I or II.

The ring opening of the epoxide is preferably carried out in an organic solvent, especially an apolar organic solvent; examples are aromatic or aliphatic hydrocarbons of appropriate boiling range, preferably toluene, xylene, mesitylene.

Examples of suitable catalysts are phase transfer catalysts, including quaternary phosphonium salts, or tertiary amines; e.g. ethyltriphenylphosphonium bromide or benzyldimethylamine.

The reaction temperature is usually in the range 80–200° C., preferably in the range 100–180° C.

For instance, a compound of the formula II in which $R_2$ is —$OR_3$ can be obtained, for example, by the following reaction schemes:

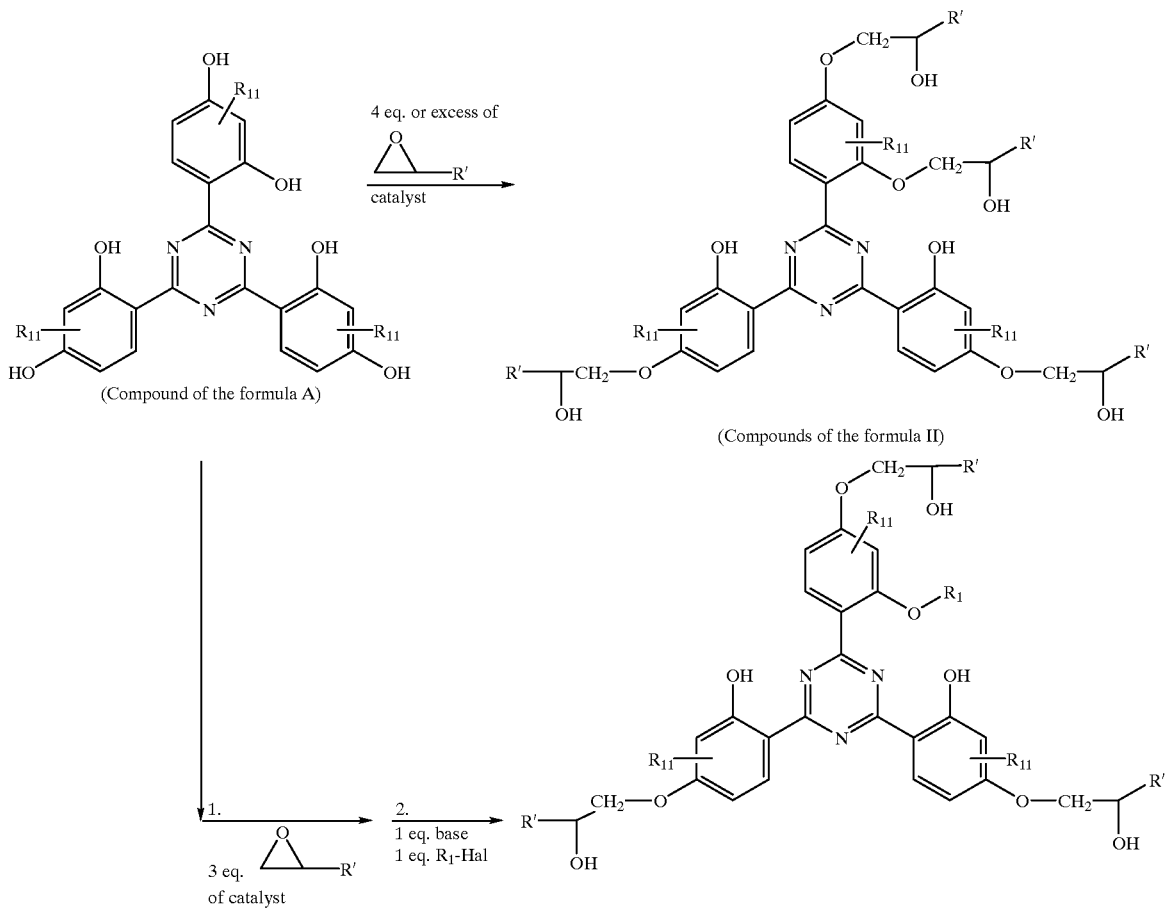

The products of the above-described reactions can be modified further by known methods in the context of the definitions given for formula I.

The reactions can be carried out in the absence of oxygen, for example by flushing with an inert gas such as argon; however, in every case oxygen does not interfere, so that the reaction can also be carried out without this measure. After the end of the reaction, the product can be worked up by common methods.

The novel compounds are particularly suitable for stabilizing organic materials against damage by light, oxygen or heat. The novel compounds are especially suitable as light stabilizers (UV absorbers).

The materials to be stabilized can, for example, be oils, fats, waxes, coating materials, cosmetics, photographic materials or biocides. Of particular interest is their use in polymeric materials as are present in plastics, rubbers, coating materials, photographic materials or adhesives. When used in cosmetic preparations, the material to be protected is frequently not the preparation itself but skin or hair to which the preparation is applied.

Examples of polymers and other substrates which can be stabilized in this way are the following:
1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
  a) radical polymerisation (normally under high pressure and at elevated temperature).
  b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The invention therefore additionally provides a composition comprising A) an organic material which is sensitive to oxidative, thermal and/or actinic breakdown/buildup and B) as stabilizer at least one compound of the formula I, and also provides for the use of compounds of the formula I stabilizing organic material against oxidative, thermal or actinic breakdown/buildup. The invention likewise embraces a method of stabilizing organic material against thermal, oxidative and/or actinic breakdown/buildup, which comprises applying or adding at least one compound of the formula I to this material.

The amount of stabilizer to be used depends on the organic material to be stabilized and on the intended use of the stabilized material. In general the novel composition contains from 0.01 to 15, especially from 0.05 to 10 and, in particular, from 0.1 to 5 parts by weight of the stabilizer (component B) per 100 parts by weight of component A). The stabilizer (component B) can be an individual compound of the formula I or else a mixture.

In addition to the compounds of the formula I the novel compositions may comprise as additional component (C) one or more customary additives, for example antioxidants, other light stabilizers, metal passivators, phosphites or phosphonites. Examples of these are the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylahenols, for example 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol.

1.3. Hydroiuinones and alkylated hydroguinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis (6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyphenyl) dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3, 3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4- hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis (3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyidiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl) phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)

benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—]$_2$ where R=3'-tert-butyl-4'-hydroxy-5'-2H-benzotriazol-2-ylphenyl, 2-[2'-hydroxy-3'-($\alpha$,$\alpha$-dimethylbenzyl)-5'-(1,1,3,3-tetramethylbutyl)-phenyl]benzotriazole; 2-[2'-hydroxy-3'-(1,1,3,3-tetramethylbutyl)-5'-($\alpha$,$\alpha$-dimethylbenzyl)-phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis (4-tert-butylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl $\alpha$-cyano-$\beta$,$\beta$-diphenylacrylate, isooctyl $\alpha$-cyano-$\beta$,$\beta$-diphenylacrylate, methyl $\alpha$-carbomethoxycinnamate, methyl $\alpha$-cyano-$\beta$-methyl-p-methoxy-cinnamate, butyl $\alpha$-cyano-$\beta$-methyl-p-methoxy-cinnamate, methyl $\alpha$-carbomethoxy-p-methoxycinnamate and N-($\beta$-carbomethoxy-$\beta$-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyidithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3, 5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1, 2,3,4-butane-tetracarboxylate, 1,1'-(1,2-ethanediyl)-bis(3,3, 5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2, 4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4, 6-trichloro-1,3,5-triazine as well as 4-butylamino-2,2,6,6-tetramethylpiperidine (CAS Reg. No. [136504-96-6]); N-(2, 2,6,6-tetramethyl-4-piperidyl)-n-dodecylsuccinimid, N-(1, 2,2,6,6-pentamethyl-4-piperidyl)-n-dodecylsuccinimid, 2-undecyl-7,7,9,9-tetramethyl-1-oxa-3,8-diaza-4-oxo-spiro [4,5]decane, a reaction product of 7,7,9,9-tetramethyl-2-cycloundecyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-$\alpha$-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1, 3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy) phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxdpropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, 6-fluoro-2,4,8,10-tetra-tert-butyl-12-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo[triethyltris(3,3', 5,5'-tetra-tert-butyl-1,1'-biphenyl-2,2'-diyl)phosphite], 2-ethylhexyl (3,3',5,5'-tetra-tert-butyl-1,1'-biphenyl-2,2'-diyl)phosphite.

Especially preferred are the following phosphites:

Tris(2,4-di-tert-butylphenyl) phosphite (Irgafos®168, Ciba-Geigy), tris(nonylphenyl) phosphite, (A)

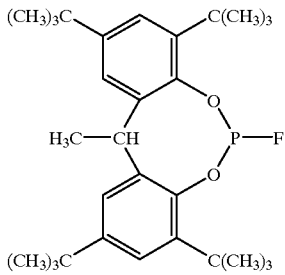

(B)

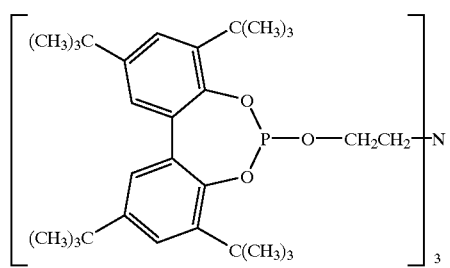

(C)

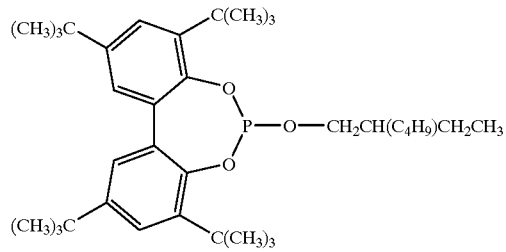

(D)

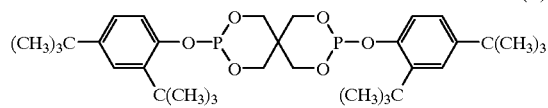

(E)

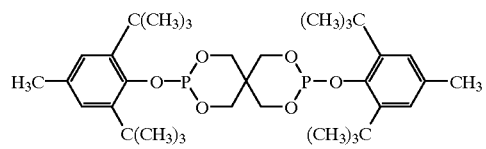

(F)

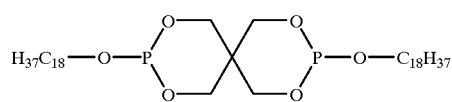

(G)

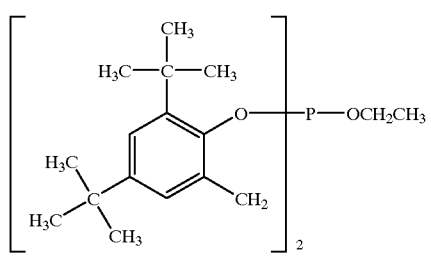

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

The nature and amount of the further stabilizers added are determined by the nature of the substrate to be stabilized and by its intended use. It is common to employ 0.1–10, for example 0.2–5% by weight, based on the material to be stabilized.

It is particularly advantageous to employ the novel compounds in combination with sterically hindered amines, for example 2,2,6,6-tetraalkylpiperidine derivatives. The invention therefore embraces a synergistic stabilizer mixture comprising (a) a compound of the formula I and (b) at least one sterically hindered amine, its salt with any desired acid or its complex with a metal, and also embraces a composition comprising A) an organic material which is sensitive to oxidative, thermal and/or actinic breakdown/buildup, B) at least one compound of the formula I, and C) a conventional additive of the type of the sterically hindered amines. Preferred sterically hindered amines are, for example, those indicated in the list above under 2.6 or those indicated below as additives to the novel coating compositions.

Of particular interest is the use of the compounds of the formula I as stabilizers in synthetic organic polymers, and corresponding compositions.

The organic materials to be protected are preferably natural, semisynthetic or synthetic organic materials. When using cosmetic preparations, the organic material to be protected is usually human or animal skin or hair.

The novel stabilizer mixtures can be employed with particular advantage in compositions which comprise as component A a synthetic organic polymer, especially a thermoplastic polymer, a binder for coatings such as, for example, paints, or a photographic material. Examples of suitable thermoplastic polymers are polyolefins, especially polyethylene (PE) and polypropylene (PP), and polymers containing heteroatoms in the main chain.

Examples of such polymers are the following classes of thermoplastic polymers:

1. Polyacetals, such as polyoxymethylene, and those polyoxymethylenes which contain comonomers such as ethylene oxide; polyacetals which are modified with thermoplastic polyurethanes, acrylates or MBS.

2. Polyphenylene oxides and sulfides and their mixtures with styrene polymers or polyamides.

3. Polyamides and copolyamides, for example those derived from diamines and dicarboxylic acids and/or from amino carboxylic acids or the corresponding lactams, such as polyamide 4, polyamide 6, polyamide 6/6, 6/10, 6/9, 6/12, 4/6, polyamide 11, polyamide 12, aromatic polyamides based on m-xylene, diamine and adipic acid; polyamides prepared from hexamethylenediamine and iso- and/or terephthalic acid with or without an elastomer as modifier, for example poly-2,4,4-trimethylhexamethyleneterephthalamide, poly-m-phenylene isophthalamide. Block copolymers of the abovementioned polyamides with polyolefins, olefin copolymers, ionomers or chemically bonded or grafted elastomers; or with polyethers, for example with polyethylene glycol, polypropylene glycol or polytetramethylene glycol. Furthermore, copolyamides or polyamides modified with EPDM or ABS; and polyamides which are condensed during processing (RIM polyamide systems).

4. Polyureas, polyimides, polyamideimides and polybenzimidazoles.

5. Polyesters, for example those derived from dicarboxylic acids and dialcohols and/or from hydroxy carboxylic acids or the corresponding lactones, such as polyethylene terephthalate, polybutylene terephthalate, poly-1,4-dimethylolcyclohexane terephthalate, polyhydroxybenzoates, and also block polyetheresters derived from polyethers having hydroxyl end groups; and also polyesters modified with polycarbonates or MBS.

6. Polycarbonates and polyestercarbonates, especially aromatic polycarbonates, for example those based on 2,2-bis(4-hydroxyphenyl)propane or 1,1-bis(4-hydroxyphenyl) cyclohexane.

7. Polysulfones, polyether sulfones and polyether ketones, especially aromatic polymers from this class.

8. Mixtures (polyblends) of such polymers with one another or with other polymers, for example with polyolefins, polyacrylates, polydienes or other elastomers as impact modifiers.

Among these, preference is given to the polycarbonates, polyesters, polyamides, polyacetals, polyphenylene oxides and polyphenylene sulfides, but especially to the polycarbonates. Polycarbonates are to be understood as meaning, in particular, those polymers whose constitutional repeating unit is of the formula—[O—A—O—CO]—, in which A is a divalent phenolic radical. Examples of A are given, inter alia, in U.S. Pat. No. 4,960,863 and in DE-A-39 22 496.

The polymers of component (A) can be linear or branched. The shaping of these polymers takes place at a relatively high temperature; polycarbonate, for example, is injection molded at 220–330° C. At these temperatures the majority of the customary light stabilizers and antioxidants are unstable and begin to break down. The abovementioned mixtures, however, are extremely temperature-stable and are therefore particularly suitable for stabilizing the polymers mentioned.

Use in multicoat systems is also of interest. In this case a novel polymer composition having a relatively high content of novel stabilizer, for example 5–15% by weight, is applied in a thin coat (10–100 µm) to a shaped article comprising a polymer which contains little or no stabilizer of the formula I. Application can take place at the same time as the shaping of the base structure, for example by coextrusion. Application can also be made, however, to the ready-shaped base structure, for example by lamination with a film or by coating with a solution. The outer coat or coats of the finished article have the function of a UV filter which protects the interior of the article against UV light. The outer coat contains preferably 5–15% by weight, in particular 5–10% by weight, of at least one compound of the formula I. The polymers stabilized in this way are notable for high weathering stability, and especially by high resistance to UV light. As a result, even when used outdoors, they retain their mechanical properties and their colour and their gloss over a long period.

Likewise particularly preferred organic materials are coating compositions and photographic material.

The invention therefore preferably also provides a composition in which the novel compound is incorporated in a thermoplastic polymer, a film-forming binder, especially one based on acrylic, alkyd, polyurethane, polyester or polyamide resin or appropriately modified resins, a photographic material or a cosmetic preparation, including a cosmetic hair preparation, for example a cosmetic or a suncream. The material to be protected (component A) can in this case be, for example, a thermoplastic polymer, a film-forming binder, especially one based on acrylic, alkyd, polyurethane, polyester or polyamide resin or appropriately modified resins, a photographic material, or human or animal skin or hair.

The use of the novel compounds as stabilizers for coatings, for example for paints, is of particular interest. The invention also therefore provides those compositions whose component A is a film-forming binder.

The novel coating composition contains preferably 0.01–10 parts by weight, especially 0.05–10 parts by weight and, in particular, 0.1–5 parts by weight of the novel stabilizer B per 100 parts by weight of solid binder A.

Multicoat systems are also possible here, in which the concentration of the compound of the formula I (component B) in the top layer can be higher, for example from 1 to 15 parts by weight, especially 3–10 parts by weight of B per 100 parts by weight of solid binder A.

The use of the compound of the formula I as a stabilizer in coatings brings with it the additional advantage that delamination, i.e. the flaking of the coating from the substrate, is prevented. This advantage is particularly manifest in the case of metallic substrates, even in the case of multicoat systems on metallic substrates.

Suitable binders (component A) are in principle all those which are customary in the art, for example those described in Ullmann's Encyclopedia of Industrial Chemistry, 5th ed., Vol. A18, pp. 368–426, VCH, Weinheim 1991. The binder is generally a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Component A can be a cold-curable or a heat-curable binder, the addition of a curing catalyst possibly being advantageous. Examples of suitable catalysts which accelerate the curing of the binder are described in Ullmann's Encyclopedia of Industrial Chemistry, Vol. A18, p.469, VCH Verlagsgesellschaft, Weinheim 1991.

Preference is given to coating compositions in which component A is a binder comprising a functional acrylate resin and a crosslinker.

Examples of coating compositions with specific binders are:

1. Paints based on cold- or heat-crosslinkable alkyd, acrylate, polyester, epoxy or melamine resins or mixtures of such resins, with or without addition of a curing catalyst;
2. two-component polyurethane paints based on hydroxyl-containing acrylate, polyester or polyether resins and on aliphatic or aromatic isocyanates, isocyanurates or polyisocyanates;
3. one-component polyurethane paints based on blocked isocyanates, isocyanurates or polyisocyanates which are deblocked in the course of stoving;
4. one-component polyurethane paints based on aliphatic or aromatic urethanes or polyurethanes and on hydroxyl-containing acrylate, polyester or polyether resins;
5. one-component polyurethane paints based on aliphatic or aromatic urethane acrylates or polyurethane acrylates having free amine groups in the urethane structure and on melamine resins or polyether resins, with or without addition of a curing catalyst;
6. two-component paints based on (poly)ketimines and on aliphatic or aromatic isocyanates, isocyanurates or polyisocyanates;
7. two-component paints based on (poly)ketimines and on an unsaturated acrylate resin or a polyacetoacetate resin or a methacrylamidoglycolate methyl ester;
8. two-component paints based on carboxyl- or amino-containing polyacrylates and polyepoxides;
9. two-component paints based on acrylate resins containing anhydride groups and on a polyhydroxy or polyamino component;
10. two-component paints based on acrylate-containing anhydrides and polyepoxides;
11. two-component paints based on (poly)oxazolines and on acrylate resins containing anhydride groups, or unsaturated acrylate resins or aliphatic or aromatic isocyanates, isocyanurates or polyisocyanates;
12. two-component paints based on unsaturated polyacrylates and polymalonates;
13. thermoplastic polyacrylate paints based on thermoplastic acrylate resins or externally crosslinking acrylate resins in combination with etherified melamine resins;
14. paint systems based on siloxane-modified or fluorine-modified acrylate resins.

The novel coating composition preferably comprises, in addition to components A and B, as component C a light stabilizer of the sterically hindered amine, 2-(2-hydroxyphenyl)-1,3,5-triazine and/or 2-hydroxyphenyl-2H-benzotriazole type, for example as set out in the above list under sections 2.1, 2.6 and 2.8. Of particular technical interest in this context is the addition of 2-monoresorcinyl-4,6-diaryl-1,3,5-triazines and/or 2-hydroxyphenyl-2H-benzotriazoles.

In order to achieve maximum light stability it is particularly advantageous to add sterically hindered amines, as set out in the above list under 2.6. The invention therefore also provides a coating composition which in addition to components A and B comprises as component C a light stabilizer of the sterically hindered amine type.

This stabilizer is preferably a 2,2,6,6-tetraalkylpiperidine derivative which comprises at least one group of the formula

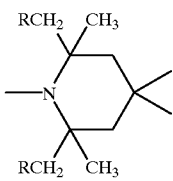

in which R is hydrogen or methyl, especially hydrogen. Component C is preferably used in an amount of 0.05–5 parts by weight per 100 parts by weight of the solid binder.

Examples of tetraalkylpiperidine derivatives which can be used as component C are given in EP-A-356 677, pages 3–17, sections a) to f). These sections of this EP-A are considered as part of the present description. It is particularly judicious to employ the following tetraalkylpiperidine derivatives:

bis-(2,2,6,6-tetramethylpiperidin-4-yl) succinate, bis-(2,2,6,6-tetramethylpiperidin-4-yl) sebacate, bis-(1,2,2,6,6-pentamethylpiperidin-4-yl) sebacate, di(1,2,2,6,6-pentamethylpiperidin-4-yl) butyl(3,5-di-tert-butyl-4-hydroxybenzyl)malonate, bis-(1-octyloxy-2,2,6,6-tetramethylpiperidin-4-yl) sebacate, tetra(2,2,6,6-tetramethylpiperidin-4-yl) butane-1,2,3,4-tetracarboxylate, tetra(1,2,2,6,6-pentamethylpiperidin-4-yl) butane-1,2,3,4-tetracarboxylate, 2,2,4,4-tetramethyl-7-oxa-3,20-diaza-21-oxodispiro [5.1.11.2]heneicosane, 8-acetyl-3-dodecyl-1,3,8-triaza-7,7,9,9-tetramethylspiro [4.5]decane-2,4-dione, 1,1-bis(1,2,2,6,6-pentamethylpiperidin-4-yl-oxycarbonyl)-2-(4-methoxyphenyl)ethene, or a compound of the formulae

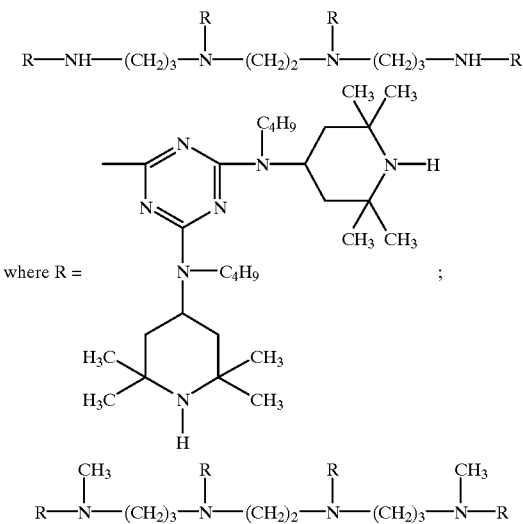

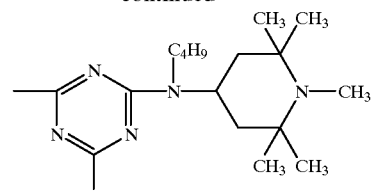

where R = 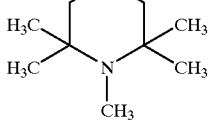

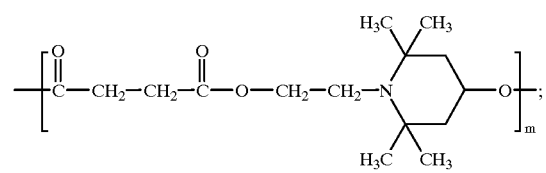

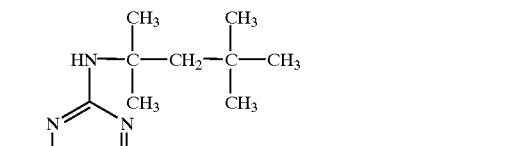

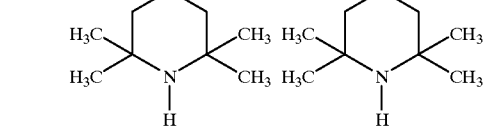

where R = 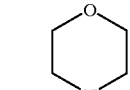

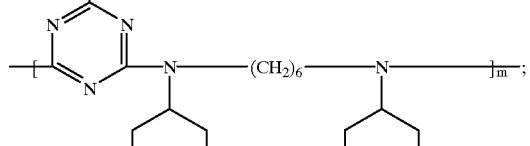

where R = 

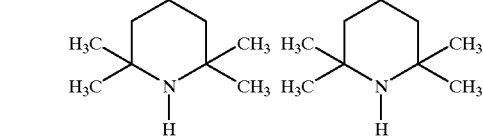

or

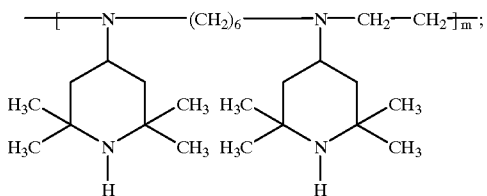

where m is 5–50.

In addition to components A, B and, if present, C, the coating composition may also comprise further components, for example solvents, pigments, dyes, plasticizers, stabilizers, thixotropic agents, drying catalysts and/or levelling assistants.

Examples of possible components are those as descibred in Ullmann's Encyclopedia of Industrial Chemistry, 5th ed., Vol. A18, pp. 429–471, VCH, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of metals Al, Ti or Zr, or organometallic compounds such as organotin compounds, for example.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminum, titanium or zirconium chelates of acetylacetone, ethyl acetylacetate, salicylaldehyde, salicylaldoxime, o-hydroxyacetophenone or ethyl trifluoroacetylacetate, and the alkoxides of these metals. Examples of organotin compounds are dibutyltin oxide, dibutyltin dilaurate or dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and their salts. Further examples are quaternary ammonium salts, for example trimethylbenzylammonium chloride.

Amino-containing resins are simultaneously binder and curing catalyst. Examples thereof are amino-containing acrylate copolymers. Phosphines, for example triphenylphosphine, can also be used as curing catalyst.

The novel coating compositions can also be radiation-curable coating compositions. In this case the binder consists essentially of monomeric or oligomeric compounds having ethylenically unsaturated bonds (prepolymers), which after application are cured, i.e. converted into a crosslinked, high molecular mass form, by actinic radiation. Where the system is a UV-curing system, it generally also includes a photoinitiator. Appropriate systems are described in the abovementioned publication Ullmann's Encyclopedia of Industrial Chemistry, 5th ed., Vol. A18, pages 451–453. In radiation-curable coating compositions the novel stabilizers can be employed even without the addition of sterically hindered amines.

The novel coating compositions can be applied to any desired substrates, for example to metal, wood, plastic or ceramic materials. In the case of the finishing of automobiles they are preferably used as topcoat. If the topcoat consists of two layers of which the lower layer is pigmented and the upper layer is not, then the novel coating composition can be used for the upper or the lower layer or for both layers, but preferably for the upper layer.

The novel coating compositions can be applied to the substrates by the customary techniques, for example by spreading, spraying, flow coating, dipping or electrophoresis; see also Ullmann's Encyclopedia of Industrial Chemistry, 5th ed., Vol.A18, pp. 491–500.

Depending on the binder system the coating c an be cured at room temperature or by heating. The coating is preferably cured at 50–150° C., powder coatings also at higher temperatures.

The coatings obtained in accordance with the invention possess an outstanding resistance to the damaging effects of light, oxygen and heat; particular mention should be made of the good light stability and weathering stability of the resulting coatings, for example paints.

The invention therefore also provides a coating, especially a paint, which is stabilized against the damaging effects of light, oxygen and heat by the addition of a compound of the formula I. The paint is preferably a topcoat for automobiles. The invention in addition comprises a process for stabilizing a coating based on organic polymers against damage by light, oxygen and/or heat, which comprises mixing with the coating composition a compound of the formula I, and provides for the use of compounds of the formula I in coating compositions as stabilizers against damage e by light, oxygen and/or heat.

The coating compositions can comprise an organic solvent or solvent mixture in which the binder is soluble. The coating composition can also be an aqueous solution or dispersion, however. The vehicle can also be a mixture of an organic solvent and water. The coating composition may also be a high-solids system or can be solvent-free (for example powder coating). Powder coatings are those, for example, as described in Ullmann's Encyclopedia of Industrial Chemistry, 5th ed., A18, pages 438–444. The powder coating can also be in the form of a powder slurry, i.e. a dispersion of the powder in—preferably—water.

The pigments can be inorganic, organic or metallic pigments. The novel coating compositions preferably contain no pigments and are used as clearcoat.

Likewise preferred is the use of the coating composition as a topcoat for applications in the automotive industry, especially as a pigmented or unpigmented top layer of the coating system. Its use for underlying coats, however, is also possible.

The novel compounds of the formula I are also particularly suitable as UV filters for protecting the skin and the hair of humans and animals against the damaging action of UV radiation. These compounds are therefore suitable as light stabilizers in cosmetic, pharmaceutical and veterinary preparations. These compounds can be used either in solution or in the micronized state.

The invention therefore additionally provides a cosmetic preparation comprising at least one compound of the formula I and cosmetically compatible excipients or auxiliaries.

For cosmetic use the novel light stabilizers, unless dissolved, usually have a mean particle size in the range from 0.02 to 2, preferably 0.05 to 1.5, and, with very particular preference, from 0.1 to $1.0\mu$. The insoluble novel UV absorbers can be brought to the desired particle size by customary methods, for example grinding with, for example, a jet, ball, vibration or hammer mill. Grinding is preferably carried out in the presence of from 0.1 to 30, preferably from 0.5 to 15% by weight, based on the UV absorber, of a grinding assistant such as, for example, an alkylated vinylpyrrolidone polymer, a vinylpyrrolidone-vinyl acetate copolymer, an acylglutamate or, in particular, a phospholipid.

In addition to the novel UV absorbers, the cosmetic compositions may also include one or more other UV protection agents, for example triazines, oxanilides, triazoles or vinyl-containing amides or cinnamamides. Such protectants are described, for example, in GB-A-2,286,774 or else are known from Cosmetics & Toiletries (107), 50 ff (1992).

The novel cosmetic compositions contain from 0.1 to 25, for example from 0.1 to 15, especially from 0.5 to 10% by weight, based on the overall weight of the compositon, of a UV absorber or a mixture of UV absorbers and a cosmetically compatible auxiliary.

The cosmetic compositions can be prepared by physical mixing of the UV absorber or absorbers with the auxiliary by customary methods, for example by simply stirring together the individual components.

The novel cosmetic compositions can be formulated as a water-in-oil or oil-in-water emulsion, as an oil-in-alcohol lotion, as a vesicular dispersion of an ionic or nonionic amphiphilic lipid, as a gel, as a solid stick or as an aerosol formulation. As a water-in-oil or oil-in-water emulsion the cosmetically compatible auxiliary contains preferably from 5 to 50% of an oil phase, from 5 to 20% of an emulsifier and from 30 to 90% of water. The oil phase in this case can be any oil suitable for cosmetic formulations, for example one or more hydrocarbon oils, a wax, a natural oil, a silicone oil, a fatty acid ester or a fatty alcohol. Preferred monools and polyols are ethanol, isopropanol, propylene glycol, hexylene glycol, glycerol and sorbitol.

Cosmetic hair compositions can be
  in the form of a shampoo, a lotion, a gel or an emulsion for rinsing, before or after shampooing, before or after dyeing or bleaching, before or after a permanent wave or before or after a straightening operation,
  in the form of a lotion, a mousse or a gel for styling or treatment,
  in the form of a lotion or a gel for brushing or for waving,
  in the form of a hair lacquer,
  in the form of a composition for permanent waving or for straightening, for dyeing or bleaching the hair.

For example, the following cosmetic hair formulations can be used:
  a$_1$) a spontaneously emulsifying stock formulation consisting of the UV absorber, PEG-6-C$_{10}$ oxo alcohol and sorbitan sesquioleate, to which water and any desired quaternary ammonium compound, for example 4% minkamidopropyl-dimethyl-2-hydroxyethylammonium chloride or quaternium 80 are added;
  a$_2$) a spontaneously emulsifying stock formulation consisting of the UV absorber, tributyl citrate and PEG-20-sorbitan monooleate, to which water and any desired quaternary ammonium compound, for example 4% minkamidopropyl-dimethyl-2-hydroxyethylammonium chloride or quaternium 80 are added;
  b) quat-doped solutions of the UV absorber in butyltriglycol and tributyl citrate;
  c) dispersions of micronized UV absorbers, obtained by known methods (precipitation from solutions or mixed solutions, grinding), having a mean diameter of 0.05–1.0 mm in APG (e.g. Plantaren) and a quat (e.g. mink-amidopropyldimethyl-2-hydroxyethylammonium chloride) in an aqueous formulation;
  d) mixtures or solutions of the UV absorber with n-alkylpyrrolidone.

The cosmetic compositions may also include further components, examples being emollients, emulsion stabilizers, skin moisteners, tanning accelerators, thickeners such as xanthan, moisture retention agents such as glycerol, preservatives, fragrances and colorants.

The novel cosmetic formulations feature excellent protection of the human skin and hair against the damaging influence of sunlight.

Other materials to be stabilized with the novel compositions are recording materials. By such materials are meant, for example, those described in Research Disclosure 1990, 31429 (pages 474–480) for photographic reproduction and other reprographic techniques.

The novel recording materials comprise, for example, those for pressure-sensitive copying systems, microcapsule photocopier systems, heat-sensitive copier systems, photographic material and ink-jet printing.

The novel recording materials feature an unexpectedly high quality, especially in terms of their light stability.

The novel recording materials have a structure which is known per se and which corresponds to the utility. They consist of a base, for example paper or plastic film, on which one or more coatings are applied. Depending on the type of material, these coats contain the suitable components required, in the case of photographic material for example silver halide emulsions, colour couplers, dyes and the like. The material intended especially for ink-jet printing has a customary base on which there is an absorption layer suitable for ink. Uncoated paper can likewise be employed for ink-jet printing; in this case, the paper functions simultaneously as a base and has the absorbent for the ink. Suitable material for ink-jet printing is described, inter alia, in U.S. Pat. No. 5,073,448, the disclosure content of which is regarded as part of the present description.

The recording material can also be transparent, for example in the case of projection films.

The compound or compounds of the formula I can be incorporated into the material even in the course of manufacture; in papermaking, for example, by addition to the pulp. Another method of use is the spraying of the material with an aqueous solution of compound(s) of the formula I, or the addition thereof to the coating.

Coatings for transparent recording materials for projection must not contain any light-scattering particles such as pigments or fillers.

The colour-binding coatings can contain further additives, for example antioxidants, light stabilizers (including UV absorbers which are not included among the novel UV absorbers), viscosity improvers, brighteners, biocides and/or antistats.

The coating is usually prepared as follows:

The water-soluble components, for example the binder, are dissolved in water and mixed. The solid components, for example fillers and other additives as already described, are dispersed in this aqueous medium. Dispersion is advantageously brought about with the aid of equipment such as ultrasonic devices, turbine agitators, homogenizers, colloid mills, bead mills, sand mills, high-speed stirrers and the like. A particular advantage of the compounds of the formula I is their ease of incorporation into the coating.

As mentioned, the novel recording materials cover a broad field of use. Compounds of the formula I can be employed, for example, in pressure-sensitive copier systems. They can be added to the paper to protect the microencapsulated dye precursors against light, or to the binder of the developer layer for protecting the dyes formed therein.

Photocopier systems with light-sensitive microcapsules which are developed by pressure are described, inter alia, in U.S. Pat. Nos. 4,416,966; 4,483,912; 4,352,200; 4,535,050; 4,5365,463; 4,551,407; 4,562,137 and 4,608,330; and also in EP-A-139,479; EP-A-162,664; EP-A-164,931; EP-A-237,024; EP-A-237,025 and EP-A-260,129. In all these systems the compounds of the formula I can be added to the colour-accepting layer. Alternatively, the compounds of the formula I can be added to the donor layer for protecting the colour formers against light.

The compounds of the formula I can also be employed in recording materials which are based on the principle of photopolymerization, photosoftening or the rupture of microcapsules, or when heat-sensitive or photosensitive diazonium salts, leuco dyes with oxidizing agent or colour lactones with Lewis acids are used.

Heat-sensitive recording material exploits the colour-imparting reaction between a colourless or weakly coloured base dye and an organic or inorganic colour developer, the recorded image being produced by heat-induced contact of the two materials. This type of heat-sensitive recording material is very widespread, not only as the recording medium for faxes, computers, etc., but also in many other fields, for example in label printing.

The heat-sensitive recording material according to the present invention is composed of a base, a heat-sensitive colour-forming recording layer on this base, and, optionally, a protective layer on the heat-sensitive, colour-forming recording layer. The heat-sensitive, colour-forming recording layer contains as its principal constituent a colour-imparting compound and a colour-developing compound, and also a compound of the formula (I). If the said protective layer is present, the compound of the formula (I) can also be incorporated into the protective layer.

Heat-sensitive recording materials are described, for example, in JP-A 8-267 915.

Further fields of use are recording materials for dye diffusion transfer printing, thermal wax transfer printing and dot matrix printing, and for use with electrostatic, electrographic, electrophoretic, magnetographic and laser-electrophotographic printers, recorders or plotters. Of the materials mentioned, preference is given to recording materials for dye diffusion transfer printing, as are described, for example, in EP-A-507,734.

Compounds of the formula I can also be employed in inks, preferably for ink-jet printing, for example those as described in U.S. Pat. No. 5,098,477, the disclosure content of which is regarded as part of the present description. The invention therefore also provides an ink comprising at least one compound of the formula I as stabilizer. The ink, especially for ink-jet printing, contains preferably water. Inks contain the stabilizer of the formula I usually in a concentration of from 0.01 to 20% by weight, in particular from 0.5 to 10% by weight.

The novel recording materials, for example photographic recording materials, also offer the advantage over materials comprising conventional UV absorbers that the UVAs of the formula (I) are required in a comparatively small amount, meaning also that the thickness of the UVA-containing layer remains low, a factor which has a positive effect, inter alia, on the imaging properties. Another advantage of the novel stabilizers is their heightened inherent stability under extreme climatic conditions, especially at high humidity and high temperature. The novel photographic material can be a black and white or a colour photographic material; colour photographic material is preferred.

Examples of colour photographic materials are colour negative films, colour reversal films, colour positive films, colour photographic paper, colour reversal photographic paper, colour-sensitive materials for the dye diffusion transfer process or the silver dye bleach process.

Examples of suitable bases for the production of colour photographic materials are films and sheets of semisynthetic and synthetic polymers, such as cellulose nitrate, cellulose acetate, cellulose butyrate, polystyrene, polyvinyl chloride, polyethylene terephthalate and polycarbonate, and paper laminated with a barytes layer or an a-olefin polymer layer (e.g. polyethylene). These bases can have been coloured with dyes or pigments, for example titanium dioxide. They can also have been coloured black for the purposes of light shielding. The surface of the base is generally subjected to a treatment for improving the adhesion of the photographic emulsion layer, for example corona discharge with subsequent application of a substrate layer.

The novel material preferably comprises the silver halide emulsion layers starting from the base, in the sequence blue-sensitive, green-sensitive and red-sensitive layer. In the novel colour photographic material the UV absorber is preferably in a layer above the green-sensitive layer, particularly preferably in a layer above the silver halide emulsion layer(s).

The novel UV absorber is preferably present in the photographic material in an amount of from 0.001 to 10 g per $m^2$, for example from 0.1 to 8 $g/m^2$, especially from 0.005 to 6 and, in particular, from 0.01 to 4 $g/m^2$.

The novel colour photographic recording material is preferably a material having the following layer sequence:

| | |
|---|---|
| a | a: Protective layer |
| b | b: Interlayer (may be absent) |
| c | c: Red-sensitive layer |
| d | d: Interlayer |
| e | e: Green-sensitive layer |
| f | f: Interlayer |
| g | g: Blue-sensitive layer |
| h | h: Base |

Another example is a material having a similar layer structure but in which layer a is absent. The novel UV absorber of the formula (I), in the layer sequence depicted, is present judiciously, for example, in at least one of layers a–e, preferably in layer a, b, c and/or d, especially in a, b and/or c, and in particular in a and/or b.

Preference is generally given to a photographic recording material comprising a compound of the formula (I) in a layer above the silver halide emulsion layer(s). Preference is also given to photographic recording material comprising at least one each of a red-sensitive and green-sensitive silver halide emulsion layer and, in between them, an interlayer, where at least one compound of the formula (I) is present in the interlayer between the red-sensitive and the green-sensitive silver halide emulsion layer. Very particularly preferred photographic recording material comprises at least one each of a red-sensitive, a green-sensitive and a blue-sensitive silver halide emulsion layer and also at least two interlayers between the aforementioned layers and a protective layer, where at least one compound of the formula (I) is present in at least one layer above the green-sensitive silver halide emulsion layer, and the silver halide emulsion layers contain dark-storage stabilizers and/or light stabilizers.

Essential constituents of the colour-photographic emulsion layers are binders, silver halide particles and colour couplers.

Of especial interest, for example, is a colour photographic recording material comprising. on a base, at least one blue-sensitive silver halide emulsion layer containing at least one yellow coupler, at least one green-sensitive silver halide emulsion layer containing at least one magenta coupler, at least one red-sensitive silver halide emulsion layer containing at least one cyan coupler, and customary top layer(s) and interlayer(s), at least one of the layers comprising a compound of the formula (I).

The photographic emulsions can be spectrally sensitized using methine dyes or other dyes. Particularly suitable dyes are cyanine dyes and merocyanine dyes, including complex merocyanine dyes.

An overview of the polymethine dyes which are suitable as spectral sensitizers, their appropriate combinations and supersensitizing combinations is given in Research Disclosure 17643 (Dec. 1978), Chapter IV.

The differently sensitized emulsion layers are allocated non-diffusing monomeric or polymeric colour couplers, which may be located in the same layer or in an adjacent layer. It is common to assign cyan couplers to the red-sensitive layers, magenta couplers to the green-sensitive layers and yellow couplers to the blue-sensitive layers.

Yellow couplers which can be used in the novel material are preferably compounds of the formula A

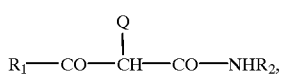

(A)

in which $R_1$ is alkyl, cycloalkyl, arylamino, anilino, a heterocyclic group or aryl, $R_2$ is aryl and Q is hydrogen or a group which can be eliminated by reaction with the oxidized developer.

Magenta couplers can, for example, be simple 1-aryl-5-pyrazolones, or pyrazole derivatives fused with 5-membered hetero-rings, for example imidazopyrazoles, pyrazolopyrazoles, pyrazolotriazoles or pyrazolotetrazoles.

Cyan couplers can, for example, be derivatives of phenol, 1-naphthol, pyrazoloazole, pyrroloazole or of pyrazoloquinazolone. One group of cyan couplers is of the formula E

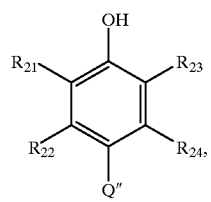

(E)

in which $R_{21}$, $R_{22}$, $R_{23}$ and $R_{24}$ are hydrogen, halogen, alkyl, carbamoyl, amino, sulfonamido, phosphoramido or ureido. $R_{21}$ is preferably H or Cl, $R_{22}$ is preferably an alkyl or amino group. $R_{23}$ is preferably an amino group and $R_{24}$ is preferably hydrogen. Q" is hydrogen (4-equivalent coupler) or a leaving group (2-equivalent coupler) which is eliminated on reaction with the oxidized developer. An exhaustive listing of cyan couplers can be found in U.S. Pat. No. 4,456,681.

The cyan couplers employed in the red-sensitive silver halide emulsion layer of the novel material are preferably of the formula

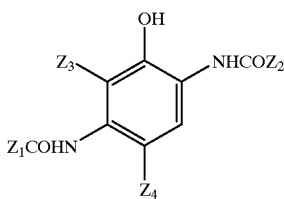

(E-12)

and/or of the formula

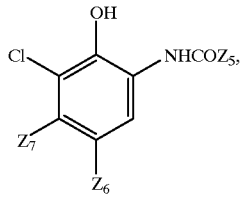

(E-13)

in which
$Z_1$ is alkyl, aryl, $Z_2$ is alkyl, cycloalkyl, aryl, a heterocyclic group or a ballast group,
$Z_3$ is hydrogen or halogen, $Z_1$ and $Z_3$ together can form a ring, and $Z_4$ is hydrogen or a leaving group, and $Z_5$ is a ballast group, Z6 is hydrogen or a leaving group and $Z_7$ is alkyl; and also those of the formulae E20 and/or E21

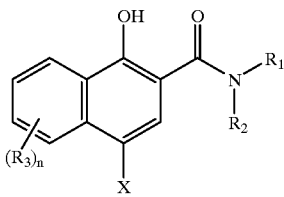

(E-20)

in which $R_1$ is preferably substituted phenyl and $R_2$ and $R_3$ are preferably H and X is preferably H or a group which is cleaved by reaction with the oxidized form of the developer, and

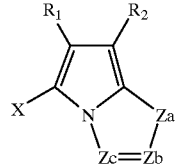

(E-21)

in which Za is —NH— or —CH($R_3$)—; Zb and Zc independently of one another are —C($R_4$)= or —N=; $R_1$, $R_2$ and $R_3$ are each an electron-attracting group having a Hammett substituent constant $\sigma_p$ of at least 0.2, with the sum of the $\sigma_p$ values of $R_1$ and $R_2$ being at least 0.65; $R_4$ is H or a substituent, and if two $R_4$s are present in the formula, they can be identical or different; and X is H or a group capable of elimination in the coupling reaction with the oxidation product of an aromatic primary amine as colour developer; or $R_1$, $R_2$, $R_3$, $R_4$ or X is a divalent group by means of which the cyan coupler is able to form a dimer or higher polymer, or to react with a polymer chain to form a homo- or copolymer.

Preference is given to a photographic material in which the red-sensitive silver halide emulsion layer comprises a cyan coupler of one of the formulae C1, C2, C3, C4, C5, C6, C7 and C8

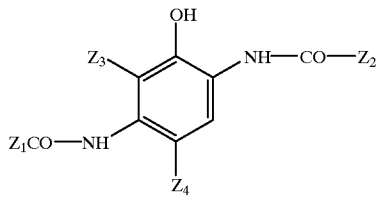
C1

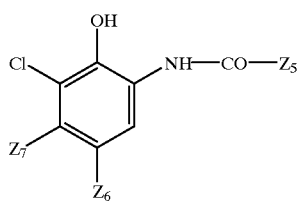
C2

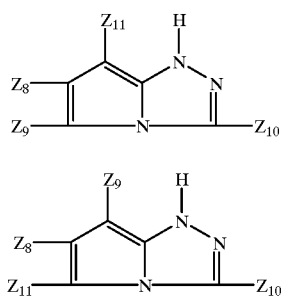
C3

C4

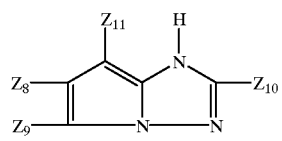
C5

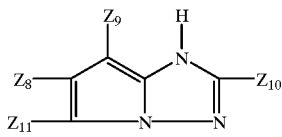
C6

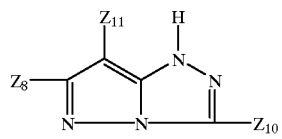
C7

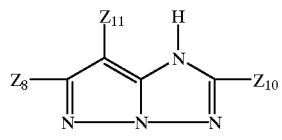
C8

in which
$Z_1$ is alkyl or aryl,
$Z_2$ is alkyl, cycloalkyl, aryl, a heterocyclic group or a ballast group,
$Z_3$ is H or halogen, or $Z_1$ and $Z_3$ together form a ring,
$Z_4$ is H or a leaving group,
$Z_5$ is a ballast group,
$Z_6$ is H or a leaving group,
$Z_7$ is alkyl,
$Z_8$ and $Z_9$ independently of one another are H or a substituent, at least one of the groups $Z_8$ and $Z_9$ being an electron-withdrawing group having a Hammett constant $(-\sigma_p)$ of 0.15 or more [$Z_8$ and $Z_9$ can be connected to one another to form a ring structure];
$Z_{10}$ is a substituent and
$Z_{11}$ is H or a leaving group.

The cyan couplers can also be connected to one another by way of the radicals $Z_8$, $Z_9$, $Z_{10}$ or $Z_{11}$ to form dimers or polymers.

Suitable leaving groups are in general those substituents which are set free after coupling with the oxidation product of a colour developer based on aromatic primary amines.

The novel photographic material preferably comprises those cyan couplers of the formulae C1–C8 in which
$Z_1$ is alkyl or aryl,
$Z_2$ is alkyl, aryl, or a ballast group,
$Z_3$ is H or halogen,
$Z_4$ is H or a leaving group,
$Z_5$ is a ballast group,
$Z_6$ is H or a leaving group,
$Z_7$ is alkyl,
$Z_8$ and $Z_9$ independently of one another are CN, $CF_3$, $COOZ_{12}$, $COZ_{12}$, $SO_2Z_{12}$, $CON(Z_{13})Z_{14}$, $SO_2N(Z_{13})Z_{14}$, and
$Z_{12}$ is unsubstituted alkyl or aryl,
$Z_{13}$ and $Z_{14}$ independently of one another are unsubstituted or substituted alkyl, aryl, heterocyclyl, alkoxy, aryloxy or heterocyclyloxy, and
$Z_{13}$ can also be H;
$Z_{10}$ embraces the definitions given for $Z_8$ and $Z_9$ or is alkyl, aryl, heterocyclyl, nitro, NH—CO—$Z_{15}$, N($Z_{15}$)$Z_{16}$, NH—CO—N($Z_{15}$)$Z_{16}$, NH—$SO_2$N($Z_{15}$), S—$Z_{15}$, NH—CO—O$Z_{15}$,
NH—$SO_2$N($Z_{15}$)$Z_{16}$, SO$Z_{15}$, and
$Z_{15}$ and $Z_{16}$ are each a substituent, and $Z_{16}$ can also be H.

The photographic layers in the novel material, especially the layers b, c and/or d in the colour photographic material described above by way of example, can preferably include further UV absorbers. Examples of such UV absorbers are benzotriazoles, 2-hydroxybenzophenones, oxanilides, cyanoacrylates, salicylic esters, acrylonitrile derivatives or thiazolines, and also conventional 2-hydroxyphenyltriazines.

Such UV absorbers are described in more detail, for example, in the following publications: U.S. Pat. Nos. 3,314,794, 3,352,681, 3,705,805, 3,707,375, 4,045,229, 3,700,455, 3,700,458, 3,533,794, 3,698,907, 3,705,805, 3,738,837, 3,762,272, 4,163,671, 4,195,999, 4,309,500, 4,431,726, 4,443,543, 4,576,908, 4,749,643, 5,500,332, 5,455,152, GB-A-1,564,089, GB-A-2,293,608, EP-A-190, 003, -747755, -717313 and JP-A-71/2784, 81/111,826, 81/27,146, 88/53,543, 88/55,542 and 96/69087. Preferred UV absorbers are benzotriazoles, especially 2-(2-hydroxyphenyl)benzotriazoles.

Preference is also given to photographic recording material comprising in addition a UV absorber, not of the formula (I), from the series of the 2-hydroxyphenyltriazines, as are described, for example, in U.S. Pat. No. 5,300,414, U.S. Pat.

No. 5,489,503, U.S. Pat. No. 5,480,108, U.S. Pat. No. 4,826,978, EP-A-706083, JP-A han 08-267915 and U.S. Pat. No. 5,364,749.

The amount of the additional UV absorber or absorbers added is judiciously within the same range as indicated above for the novel UV absorbers.

Examples of particularly suitable compounds are:

2-Hydroxyphenyltriazines of the formula

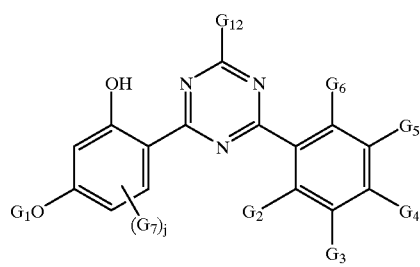

in which j is 0, 1, 2 or 3;

$G_1$ is alkyl, alkenyl or cycloalkyl;

$G_2$ and $G_6$ independently of one another are H, OH, halogen, alkyl, halomethyl, for example $CF_3$;

$G_3$, $G_5$ and $G_7$ independently of one another are H, OH, $OG_1$, halogen, alkyl, halomethyl, for example $CF_3$;

$G_4$ is H, OH, $OG_1$, halogen, alkyl, phenyl, halomethyl, for example $CF_3$, or alkenyl; and $G_{12}$ is alkyl, phenylalkyl, cycloalkyl, $OG_1$, or in particular, a group of the formula

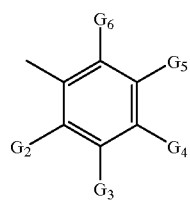

Alkyl or alkenyl substituents, or substituents which are aromatic or aliphatic ring systems, usually contain—within the context of the stated definitions—from 1 to 50 carbon atoms and can be interrupted one or more times by O, S, NR', $SO_2$, CO, phenylene, cyclohexylene, COO, OCO, —$(SiR_pR_qO)$— and/or substituted one or more times by OH, OR', NR'R", halogen, —CN, alkenyl, phenyl, —$SiR_pR_qR_r$ or COOH, where R' and R" independently of one another are H, alkyl, alkenyl or acyl, and $R_p$, $R_q$ and $R_r$ independently of one another are H, alkyl, alkenyl, phenyl, alkoxy, acyl or acyloxy.

The abovementioned groups can also carry other substituents as well. Dimers or polymers are also possible.

Preferred 2-hydroxyphenyltriazines of this class are, for example, those of the formula

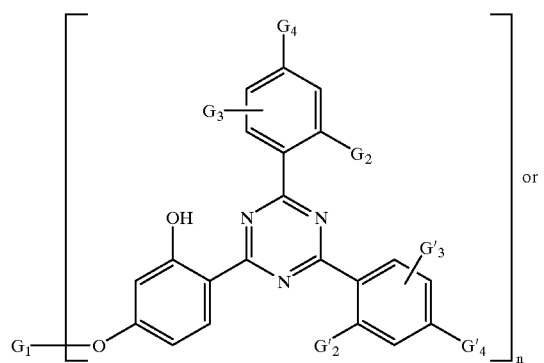

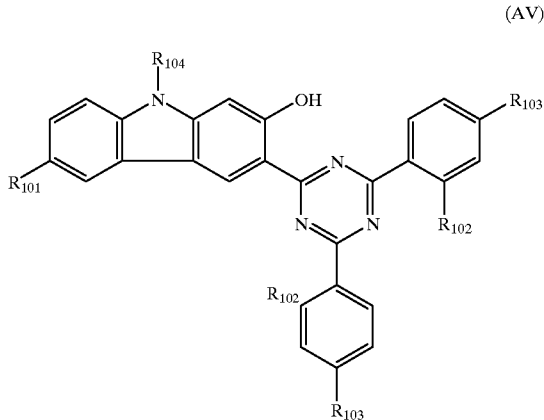

where, in formula AIII n is 1 or 2 and $G_1$, if n=1, is alkyl which is uninterrupted and unsubstituted or is interrupted by one or more O and/or substituted by one or more of the radicals OH, glycidyloxy, alkenoxy, COOH, $COOR^e$, O—CO—$R^f$, or is alkenyl, cycloalkyl, unsubstituted or OH—, Cl— or $CH_3$-substituted phenylalkyl; or $COR^g$; $SO_2$—$R^h$; $CH_2CH(OH)$—$R^i$; where $R^e$ is alkyl; alkenyl; hydroxyalkyl; alkyl or hydroxyalkyl interrupted by one or more O; cycloalkyl; benzyl; alkylphenyl; phenyl; phenylalkyl; furfuryl; or $CH_2CH(OH)$—$R^j$;

$R^f$, $R^g$ independently of one another are alkyl, alkenyl or phenyl;

$R^h$ is alkyl, aryl or alkylaryl;

$R^i$ is aralkyl or $CH_2OR^k$;

$R^k$ is cyclohexyl, phenyl, tolyl or benzyl; and $G_1$, if n=2, is alkylene; alkenylene; xylylene; alkylene or hydroxyalkylene interrupted by one or more O; hydroxyalkylene;

$G_2$ and $G'_2$ independently of one another are H, alkyl or OH;

G₄ and G'₄ independently of one another are H, alkyl, OH, alkoxy, halogen, and,
if n=1, OG₁;
G₃ and G'₃ independently of one another are H, alkyl or halogen; and
where, in formula A V,
$R_{101}$ is H, $C_1$–$C_8$alkyl, $C_1$–$C_8$alkoxy;
$R_{102}$ and $R_{103}$ independently of one another are H, halogen, OH, $C_1$–$C_8$alkyl, $C_1$–$C_8$alkoxy;
$R_{104}$ is H, OH, $C_1$–$C_8$alkyl; $C_1$–$C_8$alkoxy.

Within the scope of the stated definitions $G_1$, $G_2$, $G'_2$, $G_3$, $G'_3$, $G_4$ and $G'_4$ may also carry additional substituents, for example an ethylenically unsaturated, polymerizable group. Dimers or polymers are also possible.

Particular preference is given to colour photographic materials in accordance with the present invention, in which at least one of the layers comprises a UV absorber of the formula AIII in which
n is 1;
$G_1$ is $C_1$–$C_{12}$alkyl which is unsubstituted or substituted by OH or COOR$^e$; or is
$C_2$–$C_{12}$alkyl or $C_3$–$C_{15}$hydroxyalkyl, interrupted by one or more O; or is
$C_3$–$C_6$alkenyl; cyclohexyl; $C_7$–$C_{11}$phenylalkyl; CH₂CH(OH)—R$^j$; where
R$^e$ is $C_1$–$C_{18}$alkyl; $C_3$–$C_7$alkenyl; alkyl or hydroxyalkyl interrupted by one or more O;
$C_3$–$C_{15}$hydroxyalkyl which is interrupted by O; or is allyl, cyclohexyl or benzyl; where
R$^e$ is $C_1$–$C_{12}$alkyl; allyl; $C_3$–$C_{12}$alkyl which is interrupted by one or more O;
$G_2$ and $G'_2$ are OH;
$G_4$ and $G'_4$ are OG₁;
$G_3$ and $G'_3$ are H.

Examples of such compounds include
2,4,6-tris(2-hydroxy-4-octyloxyphenyl)-1,3,5-triazine,
2-(2,4-dihydroxyphenyl)-4,6-bis(2,4-dimethylphenyl)-1,3,5-triazine,
2,4-bis(2-hydroxy-4-propyloxyphenyl)-6-(2,4-dimethylphenyl)-1,3,5-triazine,
2-(2-hydroxy-4-octyloxyphenyl)-4,6-bis(4-methylphenyl)-1,3,5-triazine,
2-(2-hydroxy-4-dodecyloxyphenyl)-4,6-bis(2,4-dimethylphenyl)-1,3,5-triazine,
2-[2-hydroxy-4-(2-hydroxy-3-butyloxypropyloxy)phenyl]-4,6-bis(2,4-dimethylphenyl)-1,3,5-triazine,
2-[2-hydroxy-4-(2-hydroxy-3-octyloxypropyloxy)phenyl]-4,6-bis(2,4-dimethylphenyl)-1,3,5-triazine,
2-[2-hydroxy-4-(2-hydroxy-3-tridecyloxypropyloxy)phenyl]-4,6-bis(2,4-dimethylphenyl)-1,3,5-triazine;
and compounds of the following formulae:

Type (HPT-I)

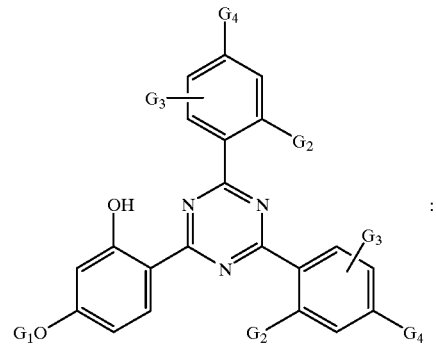

| No. | G₁ | G₂ | G₄ | G₃ |
|---|---|---|---|---|
| HPT-1 | CH₂CH(OH)CH₂O—CO—C(CH₃)=CH₂ | CH₃ | CH₃ | H |
| HPT-2 | CH₂CH(OH)CH₂OC₁₂H₂₅/C₁₃H₂₇(mixture) | CH₃ | CH₃ | H |
| HPT-3 | CH₂CH(OH)CH₂O—C₄H₉(n) | CH₃ | CH₃ | H |
| HPT-4 | CH₂COO—C₁₈H₃₇ | H | H | m-CF₃ |
| HPT-5 | C₈H₁₇ | CH₃ | CH₃ | H |
| HPT-6 | CH₂CH(OH)CH(C₂H₅)—C₄H₉(n) | CH₃ | CH₃ | H |
| HPT-6a | H | CH₃ | CH₃ | H |
| HPT-6b | CH₂CH₂OH | H | H | H |
| HPT-6c | C₈H₁₇ | H | H | H |

R$^j$ is $C_7$–$C_{12}$aralkyl or CH₂OR$^k$;
R$^k$ is cyclohexyl, phenyl, tolyl or benzyl; and
$G_2$ and $G'_2$ are OH;
$G_4$ and $G'_4$ are OG₁;
$G_3$ and $G'_3$ independently of one another are H or methyl;
especially those in which
n is 1;
$G_1$ is $C_1$–$C_{12}$alkyl which is unsubstituted or substituted by COOR$^e$; or is Type (HPT-II)

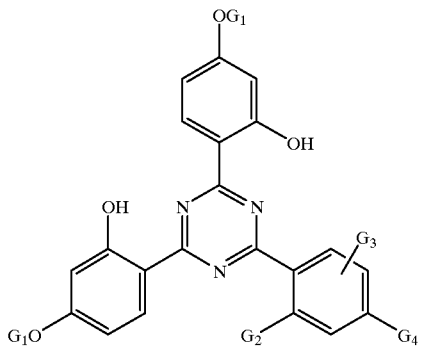

| No. | G₁ | G₂ | G₄ | G₃ |
|---|---|---|---|---|
| HPT-7 | $C_{18}H_{37}$ | $CH_3$ | $CH_3$ | o-$CH_3$ |
| HPT-8 | $CH_2CH(OH)CH_2O-C_4H_9(n)$ | H | H | H |
| HPT-9 | $CH_2CH(OH)CH_2O-C_4H_9(n)$ | $CH_3$ | $CH_3$ | H |
| HPT-10 | $CH_2CH(OH)CH_2O-C_4H_9(n)$ | $CH_3$ | $CH_3$ | o-$CH_3$ |
| HPT-11 | $CH_2CH(OH)-C_4H_9(n)$ | $CH_3$ | $CH_3$ | o-$CH_3$ |
| HPT-12 | $CH(OH)-C_5H_{11}(n)$ | $CH_3$ | $CH_3$ | o-$CH_3$ |
| HPT-13 | $C_8H_{17}$ | H | Cl | H |
| HPT-14 | $CH(CH_3)-COO-C_2H_5$ | $CH_3$ | $CH_3$ | o-$CH_3$ |
| HPT-15 | $CH_2CH(OCOCH_3)CH(C_2H_5)-C_4H_9(n)$ | H | H | H |
| HPT-16 | $CH_2CH(OH)CH(C_2H_5)-C_4H_9(n)$ | H | H | H |
| HPT-17 | $CH_2CH_2-O-CO-C(CH_3)_3$ | H | H | H |
| HPT-18 | H | H | H | H |
| HPT-19 | $(CH_2)_{10}COO-C_2H_5$ | H | Cl | H |
| HPT-20 | $(CH_2)_5COOH$ | H | H | H |
| HPT-21 | $CH_2CH(C_2H_5)-C_4H_9(n)$ | H | H | H |
| HPT-22 | $CH_2CH(OH)CH_2-O-C_4H_9(n)$ | H | t-$C_4H_9$ | H |
| HPT-23 | $CH_2CH(OH)CH_2-O-C_4H_9(n)$ | H | $OCH_3$ | H |
| HPT-24 | $(CH_2)_3-Si(CH_3)_3$ | H | H | H |

Type (HPT-III)

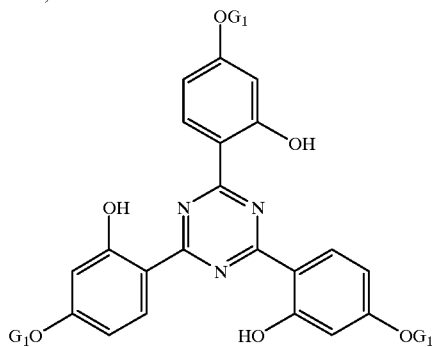

| No. | G₁ |
|---|---|
| HPT-26 | cyclohexyl |
| HPT-26a | |

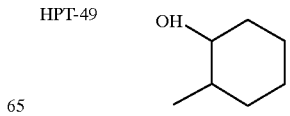

| HPT-26b | $CH_2CH(OH)CH_2-O$-2-butyl/2-pentyl (mixture) |
| HPT-27 | $CH_2CH(OH)CH_2-O-C_4H_9(n)$ |
| HPT-28 | $(CH_2)_{10}COO-C_2H_5$ |
| HPT-29 | $CH_2CH(OH)CH(C_2H_5)-C_4H_9(n)$ |
| HPT-30 | $C_4H_9$ |

-continued

Type (HPT-III)

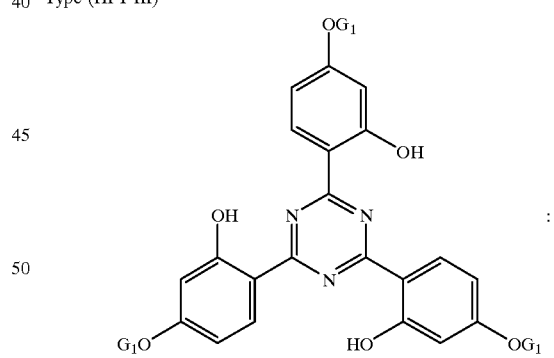

| No. | G₁ |
|---|---|
| HPT-31 | $CH_2CH(OH)CH_2-O$-ethyl/isopropyl/$C_4H_9(n)$ (mixture) |
| HPT-32 | $CH(C_3H_7)_2$ |
| HPT-33 | cyclopentyl |
| HPT-34 | $CH_2CH(OH)CH_2-O-CH_2CH_2-O-CH(CH_3)C_2H_5$ |
| HPT-49 | |

-continued
Type (HPT-III)
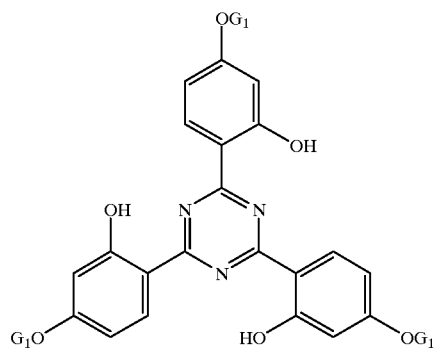
| No. | $G_1$ |
|---|---|
| HPT-50 | 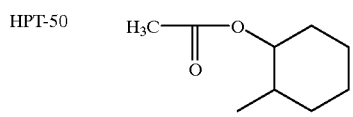 |
| HPT-51 | $C(CH_3)_2$—COO—$C_2H_5$ |
| HPT-52 | $CH(CH_3)$—COO—$C_2H_5$ |
-continued
Type (HPT-III)
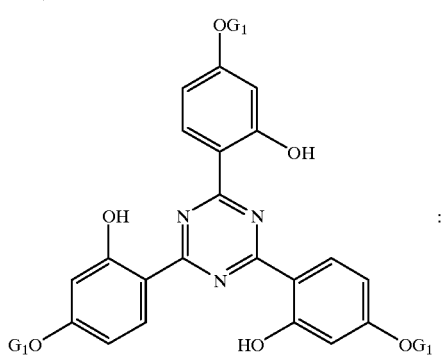
| No. | $G_1$ |
|---|---|
| HPT-53 | $CH_2CH(OH)CH_2$—O—$CH(CH_3)$—$C_2H_5/C_3H_7$ |
| HPT-54 | $(CH_2)_5$—$CH_3$ |
Type (HPT-IV)
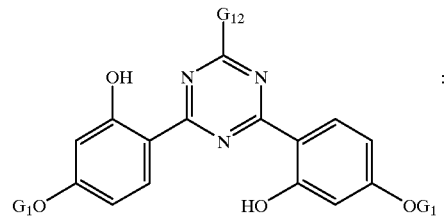
| No. | $G_1$ | $G_{12}$ |
|---|---|---|
| HPT-35 | $CH_3$ | $OCH_2CH_2OC_2H_5$ |
| HPT-36 | $CH_2CH(OCOCH_3)CH(C_2H_5)$—$C_4H_9(n)$ | $OCH_3$ |
| HPT-37 | $CH_2CH_2CH_2$—O—CO—$C_2H_5$ | $OCH_3$ |
| HPT-38 | $CH_2CH(OH)CH_2$—O—$C_4H_9(n)$ | $CH_3$ |
| HPT-39 and | $CH_2CH(OH)CH_2$—O—$C_4H_9(n)$ | $OCH_3$ |

-continued
Type (HPT-IV)
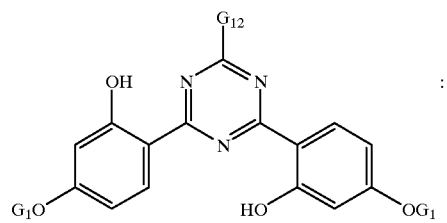
| No. | $G_1$ | $G_{12}$ |
|---|---|---|
HPT-41
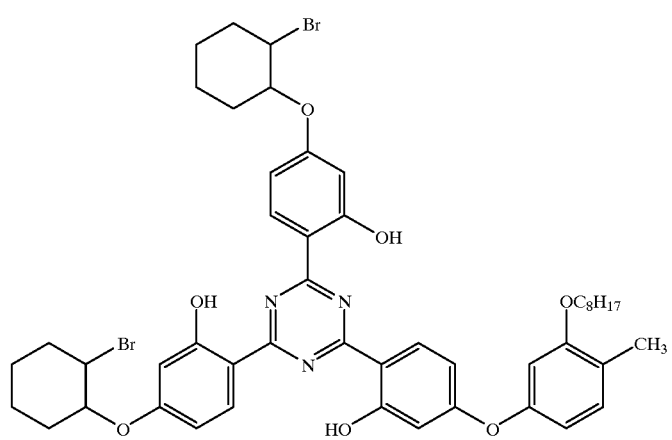
HPT-42
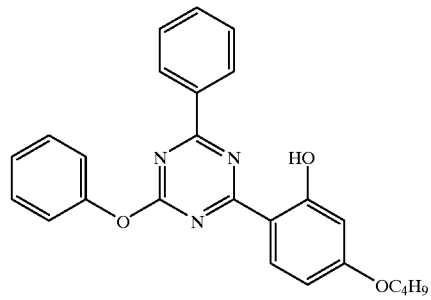

Type (HPT-V)

[Structure: carbazole with R101, R104, substituted with triazine bearing OH and two phenyl groups with R102, R103]

| No. | R$_{101}$ | R$_{102}$ | R$_{103}$ | R$_{104}$ |
|---|---|---|---|---|
| HPT-43 | H | H | H | H |
| HPT-44 | H | CH$_3$ | CH$_3$ | H |
| HPT-45 | H | OH | H | H |
| HPT-46 | H | OH | H | CH$_3$ |
| HPT-47 | H | OCH$_3$ | OCH$_3$ | H |
| HPT-48 | CH$_3$ | H | H | H |

Abbreviations used in above formulae:

i = isomer mixture; n = straight-chain radical; t = tertiary radical; o-, m- and p- denote the position of the radical relative to the triazine ring.

Benzotriazole compounds of the formula AII

[Structure AII: benzotriazole linked to phenol with OH, T$_1$, T$_2$, T$_4$ substituents and T$_3$ on benzotriazole]

(AII)

in which T$_1$ and T$_2$ independently of one another are hydrogen, halogen, alkyl, alkyl substituted by COOT$_5$, alkoxy, aryloxy, hydroxyl, aralkyl, aryl or acyloxy, where T$_5$ is alkyl or alkyl interrupted by one or more O, or T$_1$ is a group of the formula

[Structure: phenol with L$_1$, T$_4$, T$_2$ substituents linked to benzotriazole bearing T$_3$]

in which L$_1$ is a bivalent group, for example —(CH$_2$)$_n$— where n is from the range 1–8, T$_3$ is hydrogen, halogen, alkyl, alkoxy, aryloxy, acyloxy; —CF$_3$, phenyl, —S—T$_6$, —SO$_2$—T$_6$; and T$_4$ is hydrogen, hydroxyl, alkoxy, aryloxy or acyloxy or a group of one of the formulae —OCH$_2$CH(OT$_8$)—CH$_2$—O—T$_7$ or —OCH$_2$CH$_2$—O—CO—T$_7$;

T$_6$ is alkyl or aryl;

T$_7$ is alkyl or aryl;

T$_8$ is hydrogen or CO—T$_9$;

T$_9$ is alkyl or alkenyl;

and polymers prepared using these compounds. Preference is given to those compounds of the formula AII which are liquid in the temperature range around 20° C. or form a liquid phase in a mixture with other substances, especially to those in which T$_1$ and T$_2$ independently of one another are hydrogen, halogen, alkyl, alkyl substituted by COOT$_5$, alkoxy, aryloxy, hydroxyl, aralkyl, aryl or acyloxy, where T$_5$ is alkyl or alkyl which is interrupted by one or more O.

Within the scope of the stated definitions T$_1$, T$_2$, T$_3$ and T$_4$ may also carry additional substituents, for example an ethylenically unsaturated, polymerizable group. Dimers or polymers are also possible.

Especial preference is given to those compounds of the formula AII, in which

T$_1$ is H, C$_1$–C$_{12}$alkyl, 1,1-dimethylbenzyl;

T$_2$ is H, C$_1$–C$_{12}$alkyl, 1,1-dimethylbenzyl or CH$_2$CH$_2$COOT$_5$;

T$_3$ is chlorine, CF$_3$, —S—T$_6$, —SO$_2$—T$_1$;

T$_4$ is hydrogen or C$_1$–C$_{18}$alkoxy;

T$_5$ is C$_1$–C$_{18}$alkyl, or C$_3$–C$_{18}$alkyl interrupted by one or more O; and T$_6$ is phenyl.

The radicals designated as alkyl, alkenyl, aryl, arylalkyl, acyl, alkyloxy, alkenyloxy, aryloxy, arylalkyloxy and acyloxy for the conventional UV absorbers are generally those which are common in the art; preferred radicals are generally—as regards chain length, number of carbon atoms and any heteroatoms etc.—of the type as defined above for the novel compounds of the formula (I).

Examples of benzotriazoles (HBT) of the formula AII are:

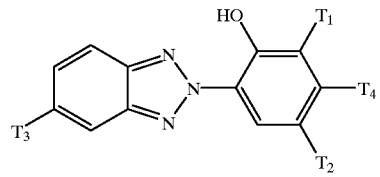

| HBT-No. | T$_1$ | T$_2$ | T$_3$ | T$_4$ |
|---|---|---|---|---|
| HBT-1 | H | CH$_3$ | H | H |
| HBT-2 | H | C(CH$_3$)$_3$ | H | H |
| HBT-3 | C(CH$_3$)$_3$ | CH$_3$ | Cl | H |
| HBT-4 | C(CH$_3$)$_3$ | C(CH$_3$)$_3$ | Cl | H |
| HBT-5 | C(CH$_3$)$_2$C$_2$H$_5$ | C(CH$_3$)$_2$C$_2$H$_5$ | H | H |
| HBT-6 | CH(CH$_3$)C$_2$H$_5$ | C(CH$_3$)$_3$ | H | H |
| HBT-7 | C(CH$_3$)$_2$—Ph | C(CH$_3$)$_2$—Ph | H | H |
| HBT-8 | C(CH$_3$)$_3$ | CH$_2$CH$_2$COOC$_8$H$_{17}$ (isomers)* | Cl | H |
| HBT-9 | C(CH$_3$)$_3$ | CH$_2$CH$_2$COOC$_8$H$_{17}$ (isomers)* | H | H |
| HBT-10 | C$_{12}$H$_{25}$ (isomers)* | CH$_3$ | H | H |
| HBT-11 | C(CH$_3$)$_2$—Ph | —C(CH$_3$)$_2$—C(CH$_3$)$_3$ | H | H |
| HBT-12 | H | H | H | O(CH$_2$)$_2$—O—CO—C(CH$_3$)=CH$_2$ |
| HBT-13 | H | H | Cl | —O—CH$_2$—CH(OCOCH$_3$)—CH$_2$—O—CO—C(CH$_3$)=CH$_2$ |
| HBT-14 | H | H | H | —O—CH$_2$—CH(OH)—CH$_2$—O—CH(C$_2$H$_5$)—C$_4$H$_9$(n) |
| HBT-15 | sec-C$_4$H$_9$ | sec-C$_4$H$_9$ | Cl | H |

*principal product

Other suitable UV absorbers are those of the formula AIII in which

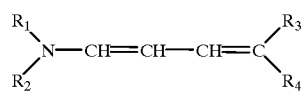
(AIII)

$R_1, R_2 = $ —C$_6$H$_{13}$(n); $R_3, R_4 = $ —CN

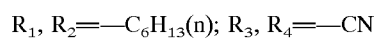

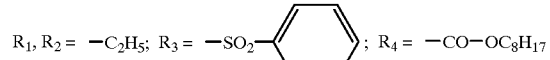

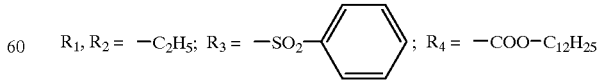

55
R$_1$, R$_2$=—CH$_2$—CH=CH$_2$; R$_3$, R$_4$=—CN
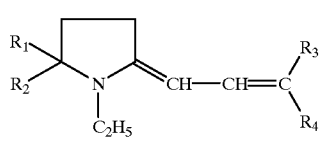
R$_1$, R$_2$=H; R$_3$=—CN; R$_4$=—CO—NHC$_{12}$H$_{25}$
56
R$_1$, R$_2$=—CH$_3$; R$_3$=—CN; R$_4$=—CO—NHC$_{12}$H$_{25}$
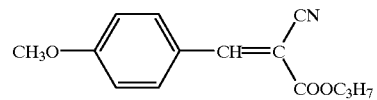
Other substances which can be used as light or dark stabilizers are described in U.S. Pat. No. 5,580,710 or U.S. Pat. No. 5,543,276.
Examples of particularly suitable compounds are:
(ST-1)
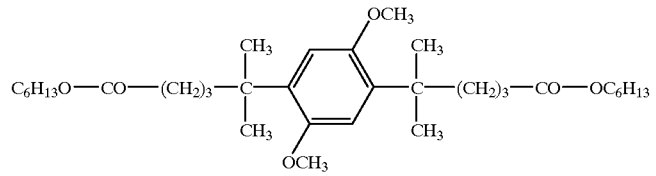
(ST-2)
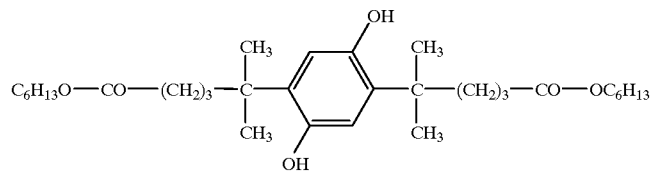
(ST-3)
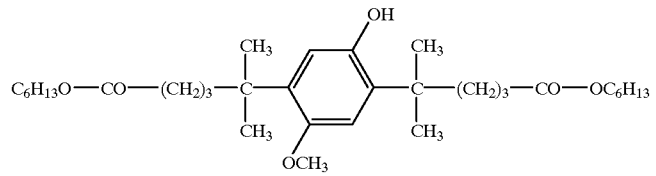
(ST-4)
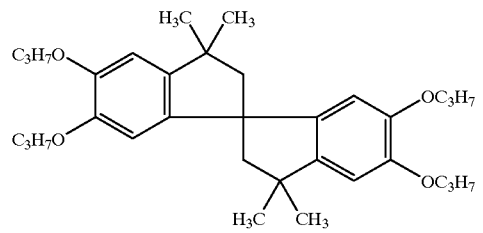
(ST-5)
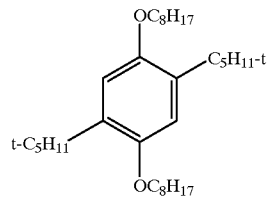
(ST-6)
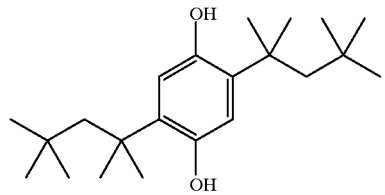

-continued
(ST-7)
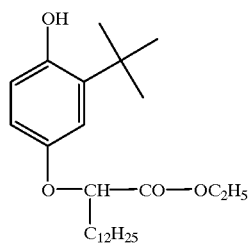
(ST-8)
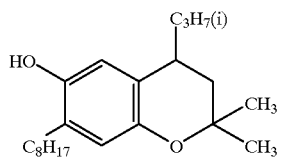
(ST-9)
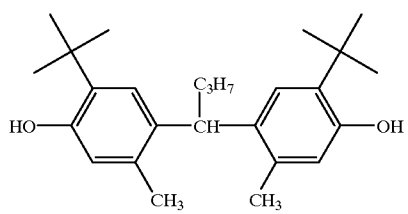
(ST-10)
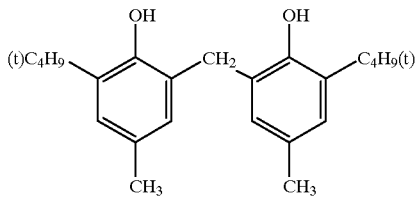
(ST-11)
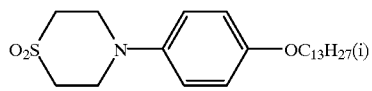
(ST-12)
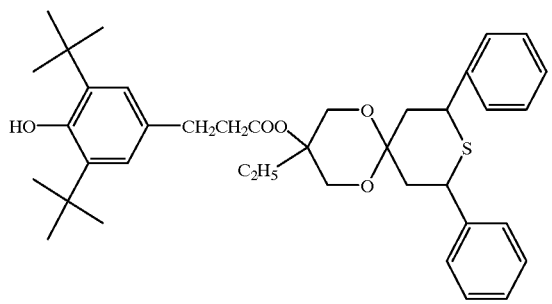
(ST-13)
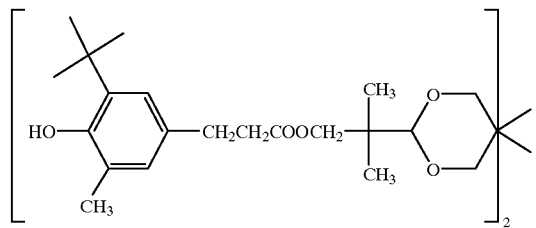

(ST-14)
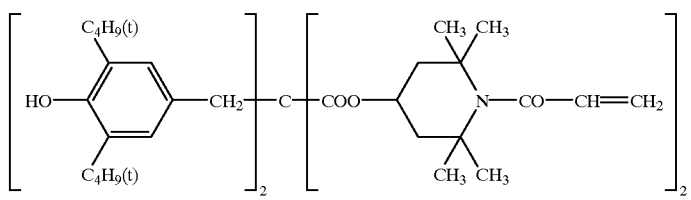
(ST-15)
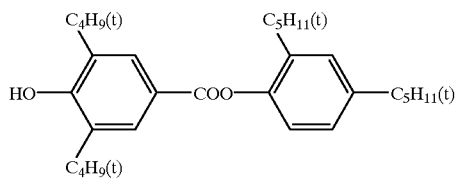
(ST-16)
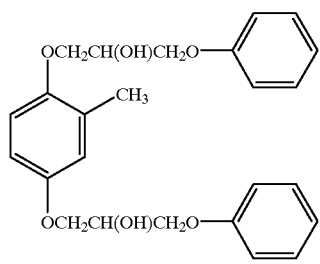
(ST-17)
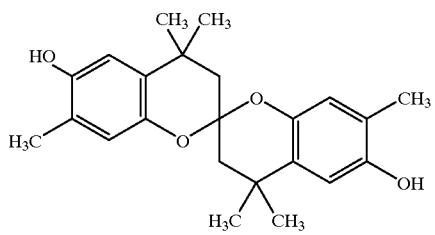
(ST-18)
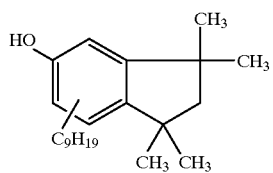
(ST-19)
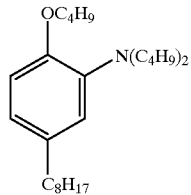

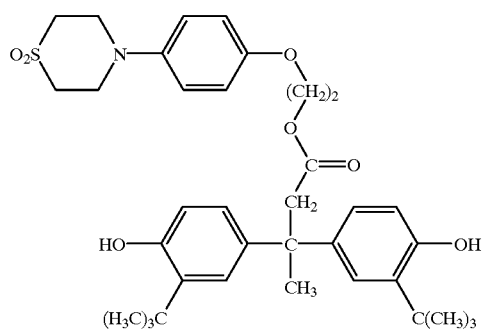
(ST-20)
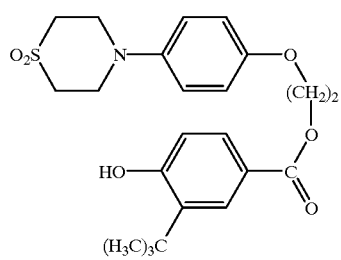
(ST-21)
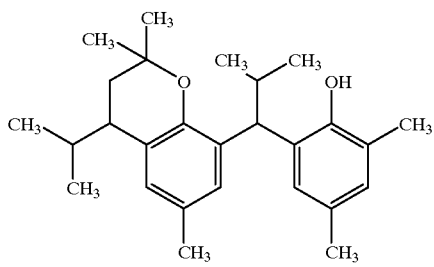
(ST-22)
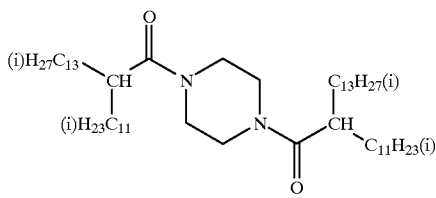
(ST-23)
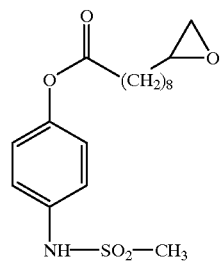
(ST-24)

(ST-25)

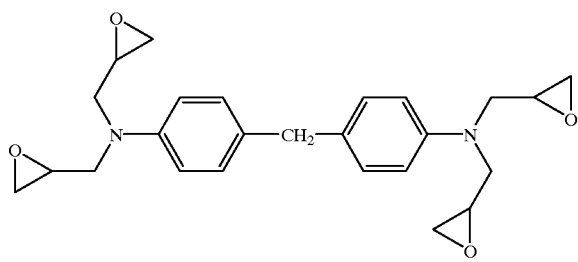

(ST-26)

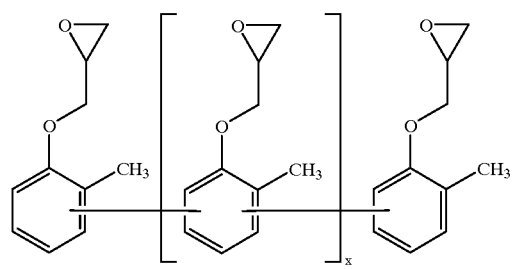

Further details on the structure of colour photographic material, and the components which can be employed in the novel material, can be found, inter alia, in U.S. Pat. No. 5,538,840, column 27, line 25, to column 106, line 16, and in the publications cited therein; these passages of U.S. Pat. No. 5,538,840 are hereby incorporated by reference. Further important components, especially couplers, are described in U.S. Pat. No. 5,578,437.

The present invention additionally provides a method of stabilizing photographic recording material comprising, on a base, at least one silver-halide emulsion layer and, if desired, at least one interlayer and/or one protective layer, which comprises adding a UV absorber of the formula (I) to at least one of the said layers.

The present invention also provides for the use of compounds of the formula (I) for stabilizing photographic recording material comprising, on a base, at least one silver halide emulsion layer and, if desired, at least one interlayer and/or one protective layer.

The preferences described earlier above in connection with the novel compounds of the formula (I) apply analogously to the novel compositions, the novel method and the novel use.

Incorporation into the organic material to be stabilized can take place, for example, by mixing or applying the compounds of the formula I and any other additives by methods customary in the art. Where the materials are polymers, especially synthetic polymers, incorporation can take place prior to or during shaping, or by applying the dissolved or dispersed compound to the polymer, with or without subsequent evaporation of the solvent. In the case of elastomers, these can also be stabilized as latices. A further option for incorporating the compounds of the formula I into polymers is to add them prior to, during or directly after the polymerization of the corresponding monomers and/or prior to crosslinking. In this context the compounds of the formula I can be added as they are or else in encapsulated form (for example in waxes, oils or polymers). In the case of addition prior to or during polymerization the compounds of the formula I may also act as a regulator of the chain length of the polymers (chain terminators).

The compounds of the formula I can also be added in the form of a masterbatch which contains this compound, for example, in a concentration of from 2.5 to 25% by weight, to the polymers that are to be stabilized.

The compounds of the formula I can judiciously be incorporated by the following methods:

as an emulsion or dispersion (e.g. to latices or emulsion polymers), as a dry mix during the mixing in of additional components or polymer mixtures, by direct addition to the processing apparatus (e.g. extruders, internal mixers etc.)

as a solution or melt.

The stabilized polymer compositions obtained in this way can be converted into shaped articles, for example into fibres, films, tapes, sheets, sandwich boards, vessels, pipes and other profiles, by the customary methods, for example by hot pressing, spinning, extrusion or injection moulding.

The invention therefore also provides for the use of the novel polymer composition for producing a shaped article.

The following table shows some typical examples of compounds of the formula I, general formula:

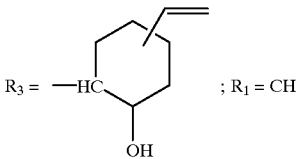

| Comp. No. | $R_3, R_1$ |
|---|---|
| 1 | $R_3 = -CH_2-CH(OH)-CH_2-O-C_4H_9$-n, $R_1 = -CH_3$ |
| 2 | $R_3 = -CH_2-CH(OH)-CH_2-O-C_4H_9$-n, $R_1 = -C_2H_5$ |
| 3 | $R_3 = R_1 = -CH_2-CH(OH)-CH_2-O-C_4H_9$-n |
| 4 | $R_3 = -CH(CH_3)-CO-O-C_2H_5$, $R_1 = -C_2H_5$ |
| 5 | $R_3 = R_1 = -CH(CH_3)-CO-O-C_2H_5$ |
| 6 | 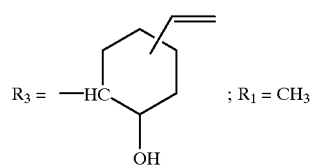 $R_3 = $ ; $R_1 = CH_3$ |
| 7 | 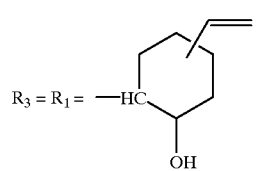 $R_3 = R_1 = $ |
| 8 | $R_3 = R_1 = C_2H_5$ |
| 9 | $R_3 = -CH_2-CH(OH)-CH_2-O-C_4H_9$-n, $R_1 = -CH(CH_3)_2$ |
| 10 | $R_3 = -CH_2-CH(OH)-CH_2-O-C_4H_9$-n, $R_1 = -CH(CH_3)-C_2H_5$ |
| 11 | $R_3 = R_1 = CH_2-CH(C_2H_5)-C_4H_9$-n |
| 12 | $R_3 = R_1 = (CH_2)_7-CH_3$ |

In compounds Nos. 6 and 7 $R_3$ is a mixture of 4-vinyl- and 5-vinyl-2-hydroxycyclohexyl.

Table continues:

| Comp. No. | $R_3$ | $R_1$ |
|---|---|---|
| 13 | n-propyl | methyl |
| 14 | n-propyl | ethyl |
| 15 | n-propyl | n-propyl |
| 16 | iso-propyl | methyl |
| 17 | iso-propyl | ethyl |
| 18 | iso-propyl | iso-propyl |
| 19 | n-butyl | methyl |
| 20 | n-butyl | ethyl |
| 21 | n-butyl | n-butyl |
| 22 | 2-butyl | methyl |
| 23 | 2-butyl | ethyl |
| 24 | 2-butyl | 2-butyl |
| 25 | n-hexyl | methyl |
| 26 | n-hexyl | ethyl |
| 27 | n-hexyl | n-hexyl |
| 28 | n-octyl | methyl |
| 29 | n-octyl | ethyl |
| 30 | n-octyl | n-octyl |
| 31 | 2-methyl-propyl | 2-methyl-propyl |
| 32 | n-pentyl | n-pentyl |
| 33 | 3-methyl-butyl | 3-methyl-butyl |
| 34 | n-heptyl | methyl |
| 35 | n-heptyl | ethyl |
| 36 | n-heptyl | n-heptyl |
| 37 | -CH2-COO-Et | ethyl |
| 38 | -CH2-COO-Et | -CH2-COO-Et |
| 39 | n-C12H25- | n-C12H25- |
| 40 | n-C16H36- | n-C16H36- |

The examples which follow illustrate the invention further. All parts or percentages, both in the examples and in the remainder of the description and in the patent claims, are by weight, unless stated otherwise. In the examples and the table, the following abbreviations are used:

Diglyme: diethylene glycol dimethyl ether

AcOEt: ethyl acetate $CHCl_3$: chloroform $CDCl_3$: deuterochloroform

DSC: differential scanning calorimetry=differential thermal analysis

ε: molar extinction coefficient $^1$H-NMR: nuclear magnetic resonance of the nuclide $^1$H $T_g$: glass transition temperature mmHg torr (1 torr=133.322 Pa)

m.p. melting point

A: PREPARATION EXAMPLES

Example A1

2,4-bis[2-hydroxy-4-(3-n-butoxy-2-hydroxypropoxy)phenyl]-6-[2-methoxy-4-(3-n-butoxy-2-hydroxypropoxy)phenyl]-1,3,5-triazine (Compound 1).

A mixture of 11.9 g (15.0 mmol) of 2,4,6-tris[2-hydroxy-4-(3-n-butoxy-2-hydroxypropoxy)phenyl]-1,3,5-triazine in 80 ml of diglyme (Fluka 99.5%) is heated under nitrogen to 80° C. To the solution there are added in succession 1.0 g (15.1 mmol) of pulverized KOH (Fluka, 85%) and 2.5 g (19.8 mmol) of dimethyl sulfate (Fluka, 99%), with stirring. After stirring at 80° C. for 20 h the mixture is cooled, the precipitate is filtered off and the solvent is stripped off from the filtrate. The crude product is purified by column chromatography (silica gel 60, 230–60 mesh, Ø=5 cm, h=30 cm;

CH₂Cl₂/methanol 95:5). Stripping the solvent from the main fraction and drying at 100° C./0.9 mmHg for 3 h give 7.0 g (57.8%) of the title compound (Compound 1).
Analysis:
$^1$H-NMR (CDCl₃, 300 MHz): The spectrum is consistent with the expected structure.
C43 H59 N3 O12 calculated: C 63.77% H 7.34% N 5.19%
(M=809.96 g/mol) found: C 63.17% H 7.58% N 5.08%
UV (AcOEt): εmax (297 nm)=35 230
εmax (346 nm)=62 370

Example A2

2,4-bis[2-hydroxy-4-(3-n-butoxy-2-hydroxypropoxy)phenyl]-6-[2,4-di-(3-n-butoxy-2-hydroxypropoxy)phenyl]-1,3,5-triazine (Compound 3).

A mixture of 20.0 g (0.049 mol) of 2,4,6-tris(2,4-dihydroxyphenyl)-1,3,5-triazine, 39.1 g (0.300 mol) of n-butyl glycidyl ether (Fluka, 97%), and 1.8 g (0.005 mol) of ethyltriphenylphosphonium bromide (Fluka, 97%) in 100 ml of mesitylene is heated under nitrogen and with stirring at 150° C. for 21 h. After cooling, the insoluble precipitate is filtered off and the solvent is stripped off from the filtrate (rotary evaporator). The residue is then dissolved in 100 ml of ethyl acetate and the solution is filtered through a silica gel bed (silica gel 60, 230–400 mesh, Ø=6 cm, h=4 cm) and eluted with 300 mL of ethyl acetate. Removal of the solvent and drying at 130° Cl. 0.1 mmHg for 2 hours gives 38.2 g (84.2% of theory) of the title product (Compound 3).
Analysis:
C49 H71 N3 O14 calculated: C 63.55 H 7.73 N 4.54%
(M=926.12 g/mol) found: C 63.55 H 7.77 N 4.51%
$T_g$=−6.1° C.
UV (AcOEt): εmax (303 nm )=35 040
εmax (350 nm )=59 850

Example A3

2,4-bis[2-hydroxy-4-(1-ethoxycarbonylethoxy) phenyl]-6-[2,4-di-(1-ethoxycarbonylethoxy)phenyl]-1,3,5-triazine (Compound 5).

A mixture of 15.0 g (0.037 mol) of 2,4,6-tris(2,4-dihydroxyphenyl)-1,3,5-triazine and 80 ml of diglyme (Fluka 99.5%) is admixed under nitrogen in succession with 9.2 g (0.139 mol) of pulverized KOH (Fluka, 85%), 0.3 g (0,002 mol of potassium iodide (Fluka, 99.5% ) and 29.5 g (0.163 mol) of ethyl 2-bromopropionate (Fluka, 98%). The mixture is heated with stirring at 108° C. for 19 h. The inorganic precipitate is filtered off hot; the solvent is removed on a rotary evaporator. The crude product is taken up in 100 ml of ethyl acetate (T=60° C. ) and the mixture is filtered through a silica gel bed (silica gel 60, 230–400 mesh, Ø=6 cm, h=4 cm) and with 300 ml of ethyl acetate.

Removal of the solvent and drying at 130° C./0.1 mmHg for 2 hours give 24.2 g of theory) of the title product: $T_g$=32.2° C.

Analysis:

C41 H47 N3 O14 calculated: C 61.10 H 5.88 N 5.21%
(M = 805.84 g/mol) found: C 60.17 H 5.67 N 5.42%
UV (AcOEt): εmax (304 nm) = 41 480
εma (355 nm) = 61 890

The following compounds are obtained by proceeding in accordance with the examples indicated in the table and using the starting materials shown:

| Comp. No. | Characterization | Example | Starting compounds |
|---|---|---|---|
| 2 | ε$_{max}$(346 nm) = 62460 | A1 | as Example A1, diethyl sulfate |
| 4 | $T_g$ = 33.7° C. | A1 | Formula A' R₃ = CH(CH₃)COOC₂H₅, diethyl sulfate |
| 6 | $T_g$ = 61.3° C. | A1 | 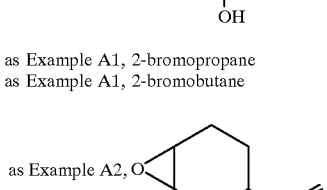 Formula A' R₃ = , dimethyl sulfate |
| 9 | $T_g$ = 56.3° C. | A1 | as Example A1, 2-bromopropane |
| 10 | $T_g$ = 79.6° C. | A1 | as Example A1, 2-bromobutane |
| 7 | $T_g$ = 78.0° C. | A2 | as Example A2, O— |
| 8 | $T_g$ = 162.9° C. | A3 | as Example A3, diethyl sulfate; |

Example A4

Preparing Compound 11 of the Formula

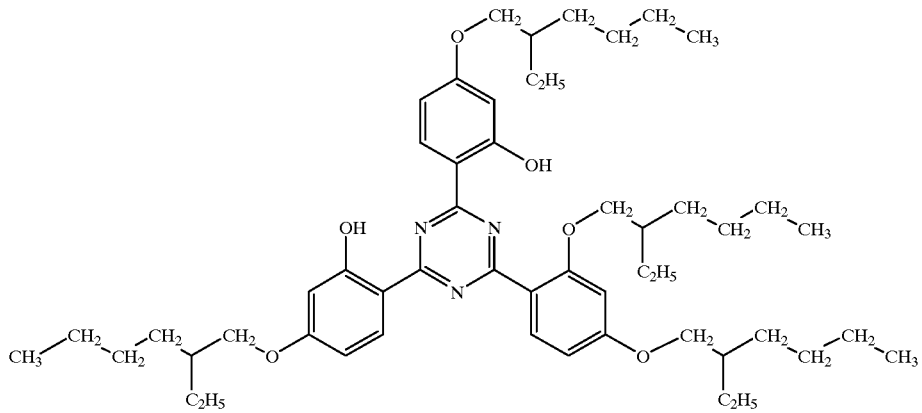

A 250 ml sulfonating flask with stirrer, dropping funnel, condenser and internal thermometer is charged with a suspension of 10.14 g (0.025 mol) of 2,4,6-tris-(2,4-dihydroxyphenyl)-1,3,5-triazine in 80 ml of dimethylformamide. The suspension is heated to 80° C., 14.5 g (0.1 mol) of dry, finely pulverized potassium carbonate are added, the temperature is raised to 125–130° C. and the mixture is stirred for one hour. Then a solution of 17.84 g (0.12 mol) of 3-(chloromethyl)heptane in 20 ml of dimethylformamide is slowly added dropwise over the course of one hour. The course of the alkylation reaction can easily be monitored by thin-layer chromatography. After 6 hours the reaction is at an end. The reaction mixture is concentrated to dryness on a rotary evaporator, the residue is taken up in 100 ml of toluene, and the mixture is filtered to remove the undissolved material. For further purification the filtrate is chromatographed over silica gel (column: Ø=5 cm, l=45 cm; eluent: toluene/cyclohexane=35/65). The title product is obtained as a tough, pale yellow resin.

UV spectrum: $\epsilon_{max}$(350 nm)=64 500 $M^{-1}cm^{-1}$ (ethanol)

$^1$H-NMR spectrum: δ [ppm, $CDCl_3$]=0.8–0.9 (m, 24H,

—$CH_3$), 1.0–1.9 (m, 36H, —$CH_2$— and —CH—), 3.7–4.0 (dd, 8H,

—O—$CH_2$—) 6.3–8.6 (9H, aromatic), 13.2–13.7 (ss, 2H, —OH)

If 3-(chloromethyl)heptane in the procedure described above is replaced by the compound 1-chlorooctane, the compound of the formula

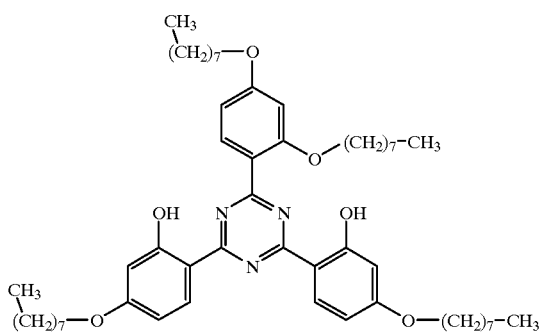

(Compound 12) is obtained as pale yellow crystals of m.p. 65–66° C.

Example A5

Preparation of Intermediates of the Formula

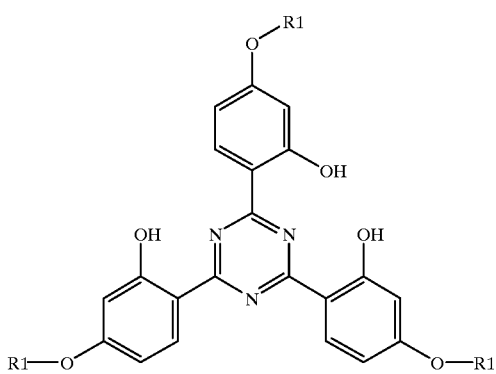

Compound R1

Int. 1.: iso-propyl
Int. 2.: n-butyl
Int. 3.: n-hexyl
Int. 4.: n-heptyl
Int. 5.: n-octyl Int. 6.: —CH2—COO—C2H5

Int. 7.: n-propyl

Int. 8.: 2-butyl a) 2,4,6-Tris(2'-hydroxy-4'-isopropyloxyphenyl)-1,3,5-triazine (Comp. int. 1) The reaction is carried out in a 1 l steel autoclave with mechanical stirrer.

A mixture of 50.0 g (0.123 mol) of 2,4,6-tris(2',4'-dihydroxyphenyl)-1,3,5-trazine, 54.6 g (0.395 mol) of potassium carbonate, 1.0 g (0.006 mol) of potassium iodide (Merck, 99.0%) and 50.1 g (0.407 mol) of isopropyl bromide (Fluka, 99.0%) in 200 ml of diethylene glycol dimethyl ether (Diglyme, Merck, >99%) is held with stirring at 140° C. under a pressure of 3.8 bar for 24 h. After cooling, it is heated to 100° C. and filtered. The filter cake is subjected to extraction at 30° C. with 500 ml of methylene chloride. After refiltration the filtrate is evaporated and the solid residue is dried at 60° C./50 mmHg for 24 h. This gives 30.5 g of 2,4,6-tris(2'-hydroxy-4'-isopropyloxyphenyl)-1,3,5-triazine (Comp. int. 1) as a yellow solid of m.p. 122° C. (DSC).

The Comp. int. 2. is obtained analogously, m.p. 142–145° C.

b) 2,4,6-Tris(2'-hydroxy-4'-n-hexyloxyphenyl)-1,3,5-triazine (Comp. int. 3).

Under nitrogen, a mixture of 81.1 g (0.200 mol) of 2,4,6-tris(2',4'-dihydroxyphenyl)-1,3,5-triazine, 87.1 g (0.630 mol) of potassium carbonate (Merck, 99.0%) and 111.2 g (0.660 mol) of 1-bromohexane (Fluka, 98%) in 1.5 l of diethylene glycol dimethyl ether (Diglyme, Merck, >99%) is stirred at 120° C. for 20 h.

After hot filtration and cooling the precipitate is filtered off and recrystallized from 2.5 l of ethyl acetate, giving 46.0 g of 2,4,6-tris(2'-hydroxy-4'-n-hexyloxyphenyl)-1,3,5-triazine (Comp. int. 3) of m.p. 148–150° C.

The following compounds are obtained analogously:

int.4 (m.p. 75–102° C.); int.5 (m.p. 125–127° C.); int.6 (m.p. 153–159° C.).

Example A6

2,4-bis(2'-hydroxy-4'-isopropyloxyphenyl)-6-(2'-methoxy-4'-isopropyloxyphenyl)-1,3,5-triazine (Compound No. 16).

Under nitrogen, a mixture of 10.6 g (0.020 mol) of 2,4,6-tris(2'-hydroxy-4'isopropyloxyphenyl)-1,3,5-triazine (int. 1) and 1.3 g (0.020 mol) of pulverized KOH (Fluka, 85%) in 80 ml of 1,2-dimethoxy ethane (Fluka, 99%) is stirred at 60° C. 3.3 g (0.026 mol) of dimethyl sulfate (Fluka, 99.0%) are added to the clear, dark orange-coloured solution.

The mixture is held at 76° C. for 21 h. After cooling, it is poured into 500 g of an ice/water mixture and stirred for 30 minutes. The precipitate is filtered off and dried at 60°/50 mmHg for 14 h. It is subsequently recrystallized from 160 ml of 2-methoxyethanol to give 9.6 g of 2,4-bis(2'-hydroxy-4'-isopropyloxyphenyl)-6-(2'-methoxy-4'-isopropyloxyphenyl)-1,3,5-triazine (Comp. 16) of m.p. 185–188° C.

Example A7

2,4-bis(2'-hydroxy-4'-isopropyloxyphenyl)-6-(2'-ethoxy-4'-isopropyloxyphenyl)-1,3,5-triazine (Comp. No. 17)

Under nitrogen, a mixture of 10.6 g (0.020 mol) of 2,4,6-tris(2'-hydroxy-4'-isopropyloxyphenyl)-1,3,5-triazine (int. 1) and 1.3 g (0.020 mol) of pulverized KOH (Fluka, 85%) in 80 ml of 1,2-dimethoxyethane (Fluka, 99%) is stirred at 50° C. 4.0 g (0.026 mol) of diethyl sulfate (Fluka, 99.0%) are added to the clear, dark orange-coloured solution.

The mixture is held at reflux temperature (85° C.) with stirring for 21 h. After cooling, it is poured into 500 g of an ice/water mixture, stirred for 1 h and subjected to extraction with 1 l of methylene chloride. The extract is dried (MgSO$_4$). Removal of the solvent gives the crude product as a pale yellow solid. Recrystallization from 120 ml of 2-methoxyethanol gives 9.4 g of 2,4-bis(2'-hydroxy-4'-isopropyloxyphenyl)-6-(2'-ethoxy-4'-isopropyloxyphenyl)-1,3,5-triazine (Comp. No. 17) of m.p. 163–167° C.

Example A8

2,4-bis(2'-hydroxy-4'-isopropyloxyphenyl)-6-(2',4'-diisopropyloxyphenyl)-1,3,5-triazine (Compound 18).

The reaction is carried out in a 1 l steel autoclave with mechanical stirrer.

A mixture of 40.5 g (0.100 mol) of 2,4,6-tris(2',4'-dihydroxyphenyl)-1,3,5-triazine, 59.4 g (0.430 mol) of potassium carbonate, 1.0 g (0.006 mol) of potassium iodide (Merck, 99.0%) and 54.1 g (0.440 mol) of isopropyl bromide (Fluka, 99.0%) in 200 ml of diethylene glycol dimethyl ether (Diglyme, Merck, >99%) is stirred at 140° C. and from 4.0 to 5.0 bar for 24 h. After cooling, 800 ml of methylene chloride are added and stirring is continued for 20 minutes at 40° C. The solid is filtered off and the filtrate is concentrated by evaporation. Recrystallization from 180 ml of 2-methoxyethanol gives 43.4 g of 2,4-bis(2'-hydroxy- 4'-isopropyloxyphenyl)-6-(2',4'-diisopropyloxyphenyl)-1,3,5-Compound 18) of m.p. 159–166° C.

Example A9

2,4-bis(2'-hydroxy-4'-n-hexyloxyphenyl)-6-(2',4'-di-(n-hexyloxy)phenyl)-3,5-triazine (Compound 27).

Under nitrogen, a mixture of 60.8 g (0.150 mol) of 2,4,6-tris(2',4'-dihydroxyphenyl)-1,3,5-triazine and 87.1 g (0.630 mol) of potassium carbonate in 700 ml of 2-ethoxyethane (Fluka, 99.5%) is added dropwise over the course of 15 minutes to 134.8 (0.800 mol) of 1-bromohexane (Fluka, 98%) which is held at 80° C. The mixture is subsequently heated at 120° C. for 20 h. After cooling, the reaction mixture is poured into 8 l of cold water. After 24 hours at 25° C. the precipitate is filtered off, washed with water (300 ml) and dried. The crude product is chromographed [2.5 kg of silica gel 60 (230–400 mesh), Ø=13 cm; h=60 cm; eluted with hexane/ethyl acetate (39:1)]. Removal of the solvent from the main fraction gives 69.2 g of 2,4-bis(2'-hydroxy-4'-n-hexyloxyphenyl)-6-(2',4'-di(n-hexyloxy)phenyl)-1,3,5-triazine (Compound 27) of m.p. 85–87° C.

The following compounds are obtained by following the procedure of the examples indicated in the table and using the starting materials shown:

| Comp. No. | Characterization | Example | Starting compound |
|---|---|---|---|
| 13 | | A6 | int. 7 |
| 14 | | A7 | int. 7 |
| 15 | m.p. 149–152° C. | A8 | 1-bromopropane |
| 19 | m.p. 118–122° C. | A6 | int. 2 |
| 20 | m.p. 90–92° C. | A7 | int. 2 |
| 21 | m.p. 93–98° C. | A8 | 1-bromobutane |
| 22 | | A6 | int. 8 |
| 23 | | A7 | int. 8 |
| 24 | $\epsilon$(349nm, AcOEt): 58560 | A8 | 2-bromobutane |
| 25 | m.p. 116–117° C. | A6 | int. 3 |
| 26 | m.p. 75–78° C. | A7 | int. 3 |
| 28 | m.p. 95–96° C. | A6 | int. 5 |
| 29 | m.p. 69–71° C. | A7 | int. 5 |
| 30 | | A9 | 1-bromooctane |
| 31 | m.p. 122–132° C. | A8 | 1-bromo-2-methylpropane |
| 32 | m.p. 72–77° C. | A8 | 1-bromopentane |
| 33 | m.p. 95–106° C. | A8 | 1-bromo-3-methylbutane |
| 34 | m.p. 55° C. (DSC) | A6 | int. 4 |
| 35 | m.p. 42° C. (DSC) | A7 | int. 4 |
| 36 | m.p. 50–62° C. | A9 | 1-bromoheptane |
| 37 | m.p. 134–155° C. | A7 | int. 6 |
| 38 | m.p. 148-165° C. | A9 | $BrCH_2COOC_2H_5$ |
| 39 | m.p. 48° C. (DSC) | A9 | 1-bromododecane |
| 40 | m.p. 51.2° C. (D)SC) | A9 | 1-bromohexadecane |

B USE EXAMPLES

Example B1

Light Stabilization of Polypropylene Fibres 2.5 g of the novel stabilizer from Examples A1, A2 or A3 are mixed together with 1 g of tris(2,4-di-tert-butylphenyl) phosphite, 1 g of calcium monoethyl 3,5-di-tert-butyl-4-hydroxybenzylphosphonate, 1 g of calcium stearate and 2.5 g of $TiO_2$ (Kronos RN 57) in a turbine agitator with 1000 g of polypropylene powder (melt index 12 g/10 min, measured at 230° C./2.16 kg). The mixtures are extruded at 200–230° C. to granules; these granules are subsequently processed to fibres using a pilot plant (Leonard; Sumirago/VA, Italy) under the following conditions:

Extruder temperature: 190–230° C.
Head temperature: 255–260° C.
Draw ratio: 1:3.5
Drawing temperature: 100° C.
Fibres: 10 den The fibres prepared in this way are exposed against a white background in a Weather-O-Meter® Type 65 WR (Atlas Corp.) with a black standard temperature of 63° C. in accordance with ASTM D 2565-85. After different exposure times the residual tensile strength of the samples is measured. From the measurements the exposure time $T_{50}$ after which the tensile strength of the samples has fallen to half its signal level is calculated.

For comparison purposes, fibres without novel stabilizer are produced and tested under otherwise identical conditions. The fibres stabilized in accordance with the invention exhibit outstanding strength retention.

Example B2

Stabilization of a Two-coat Paint System

The novel stabilizer is incorporated into 5–10 g of xylene and is tested in a clearcoat of the following composition:

| | |
|---|---|
| Synthacryl ® C 303[1] | 27.51 g |
| Synthacryl ® SC 370[2] | 23.34 g |
| Maprenal ® MF 650[3] | 27.29 g |
| Butyl acetate/butanol (37/8) | 4.33 g |
| Isobutanol | 4.87 g |
| Solvesso ® 150[4] | 2.72 g |
| Crystal oil K-30[5] | 8.74 g |
| Levelling assistant Baysil ® MA[6] | 1.20 g |
| | 100.00 g |

[1]Acrylate resin from Hoechst AG; 65% solution in xylene/butanol 26:9
[2]Acrylate resin from Hoechst AG; 75% solution in Solvesso ® 100[4]
[3]Melamine resin from Hoechst AG; 55% solution in isobutanol
[4]manufacturer: ESSO
[5]manufacturer: Shell
[6]1% in Solvesso ® 150; manufacturer: Bayer AG 1% of the stabilizer indicated in Table B2 (in xylene) is added to the clearcoat, based on the solids content of the coating material. The comparison used is a clearcoat containing no light stabilizer.

The clearcoat is diluted with Solvesso® 100 to spray viscosity and is sprayed onto a prepared aluminum panel (Uniprime®, light green metallic basecoat) and stoved at 130° C. for 30 minutes, to give a dry film thickness of 40–50 mm of clearcoat.

The samples are then weathered in an UVCON® weathering instrument from Atlas Corp. (UVB-313 Lamps) with a cycle of 8 h of UV irradiation at 70° C. and 4 h of condensation at 50° C.

The surface gloss (20° gloss, DIN 67530) of the samples is measured at regular intervals. The results are compiled in the table below.

Tab. B2: 20° gloss (DIN 67530) before beginning and after UVCON® weathering 20° gloss after

| Stabilizer | 0 h | 1200 h | 1600 h | of weathering |
|---|---|---|---|---|
| none | 86 | 41 | 19* | |
| Comp. 1 | 85 | 86 | 85 | |
| Comp. 3 | 87 | 87 | 86 | |
| Comp. 11 | 86 | 87 | 86 | |

*Cracking

The samples with the novel stabilizer exhibit high weathering stability and resistance to cracking.

Example B3

Facility for Incorporation into Photographic Layers

A gelatin coat of the following composition (per $m^2$) is applied in the customary manner to a polyester base.

| Components: | Amount: |
|---|---|
| Gelatin | 1200 mg |
| Tricresyl phosphate | 510 mg |
| Hardener | 40 mg |
| Wetting agent | 100 mg |
| Comp. of formula I | 400 mg |

The hardener is: potassium salt of 2-hydroxy-4,6-dichloro-1,3,5-triazine. The wetting agent is sodium 4,8-diisobutyinaphthalene-2-sulfonate.

The gelatin coats are dried at 20° C. for 7 days.

When the novel compound 2 is used, clear transparent coats are obtained which are suitable for a photographic recording material for example as a UV filter coat.

Example B4

A polyethylene-coated Base Material is Coated with a Gelatin Coat Comprising Silver Bromide and Magenta Coupler (M-9) of the Formula

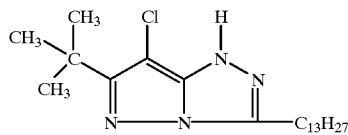

The gelatin coat includes the following components (per m² of base material):

| Component | AgBr coat |
|---|---|
| Gelatin | 5.15 g |
| Hardener | 300 mg |
| Wetting agent | 85 mg |
| Silver bromide | 260 mg |
| Magenta coupler | 325 mg |
| Tricresyl phosphate | 162 mg |

The hardener used is the potassium salt of 2,4-dichloro-6-hydroxytriazine; the wetting agent used is the sodium salt of diisobutylnaphthalenesulfonic acid.

A step wedge having a density difference of 0.3 log E per step is exposed onto each of the resulting samples, which are then processed in accordance with the manufacturer's instructions in the P94 processing process of Agfa Gevaert for negative colour papers.

After exposure and processing, the density of reflectance in the green region for the magenta stage is measured at a density of between 0.9 and 1.1 of the wedge.

A UV absorber filter comprising the compound 11 is prepared on transparent base material as described in Example B3.

The wedge is subsequently exposed behind the UV absorber filter in an Atlas exposure instrument at 15 kJ/cm² and the reflectance density is measured again. The magenta dye density loss (-ΔD) is greatly reduced by the compound 11 as stabilizer in comparison with the sample containing no stabilizer.

Example B5

The procedure described in Example B3 is repeated but using a mixture of 2 parts by weight of the compound No. 1 and 1 part by weight of HPT 7. Clear transparent coats are obtained which are suitable for a photographic recording material.

Example B6

A photographic material having the following layer structure is produced:

| |
|---|
| top layer |
| red-sensitive layer |
| second gelatine interlayer |
| green-sensitive layer |
| first gelatine interlayer |
| blue-sensitive layer |
| polyethylene base |

The gelatin layers consist of the following components (per m² of base material):

Blue-sensitive Layer
  α-(3-benzyl-4-ethoxyhydantoin-1-yl)-α-pivaloyl-2-chloro-5-[α-(2,4-di-tamylphenoxy)butanamido]acetanilide (400 mg)
  α-(1-butylphenylurazol-4-yl)-α-pivaloyl-5-(3-dodecanesulfonyl-2-methylpropanamido)-2-methoxyacetamide (400 mg)
  Dibutyl phthalate (130 mg)
  Dinonyl phthalate (130 mg)
  Gelatin (1200 mg)
  1,5-Dioxa-3-ethyl-3-[β-(3,5-di-t-butyl-4-hydroxyphenyl)propionyloxymethyl]-8,10-diphenyl-9-thia[5.5]spiroundecane (150 mg)
  bis(1-acryloyl-2,2,6,6-tetramethyl-4-piperidyl) 2,2-bis(3,5-di-t-butyl-4-hydroxybenzyl)malonate (150 mg)
  3,5-di-t-butyl-4-hydroxy(2,4-di-t-amylphenyl)benzoate (150 mg)
  poly(N-t-butylacrylamide) (50 mg)
  blue-sensitive silver chlorobromide emulsion (240 mg)
First Gelatin Interlayer
  gelatin (1000 mg)
  2,5-di-t-octylhydroquinone (100 mg)
  hexyl 5-[2,5-dihydroxy-4-(4-hexyloxycarbonyl-1,1-dimethylbutyl)phenyl]-5-methylhexanoate (100 mg)
  dibutyl phthalate (200 mg)
  diisodecyl phthalate (200 mg)
Green-sensitive Layer
  7-chloro-2-{2-[2-(2,4-di-t-amylphenoxy)octanamido]-1-methylethyl}-6-methyl-1H-pyrazolo[1,5-b][1,2,4]triazole (100 mg)
  6-t-butyl-7-chloro-3-(3-dodecanesulfonylpropyl)-1H-pyrazolo[5,1-o][1,2,4]triazole (100 mg)
  dibutyl phthalate (100 mg)
  dicresyl phosphate (100 mg)
  trioctyl phosphate (100 mg)
  gelatin (1400 mg)
  3,3,3',3'-tetramethyl-5,5',6,6'-tetrapropoxy-1,1'-spirobilndane (100 mg)
  4-(i-tridecyloxyphenyl)thiomorpholine 1,1-dioxide (100 mg)

4,4'-butylidenebis(3-methyl-6-t-butylphenol) (50 mg)
2,2'-isobutylidenebis(4,6-dimethylphenol) (10 mg)
3,5-dichloro-4-(hexadecyloxycarbonyloxy)ethylbenzoate (20 mg)
3,5-bis[3-(2,4-di-t-amylphenoxy)propylcarbamoyl] sodium benzenesulfinate (20 mg)
green-sensitive silver chlorobromide emulsion (150 mg)

Second Gelatin Interlayer
gelatin (1000 mg)
5-chloro-2-(3,5-di-t-butyl-2-hydroxyphenyl)benzo-1,2,3-triazole (200 mg)
2-(3-dodecyl-2-hydroxy-5-methylphenyl)benzo-1,2,3-triazole (200 mg) trinonyl phosphate (300 mg)
2,5-di-t-octylhydroquinone (50 mg)
hexyl 5-[2,5-dihydroxy-4-(4-hexyloxycarbonyl-1,1-dimethylbutyl)phenyl]-5-methylhexanoate (50 mg)

Red-sensitive Layer
2-[α-(2,4-di-t-amylphenoxy)butanamido]-4,6-di-chloro-5-ethylphenol (150 mg)
2,4-dichloro-3-ethyl-6-hexadecanamidophenol (150 mg)
4-chloro-2-(1,2,3,4,5-pentafluorobenzamido)-5-[2-(2,4-di-t-amylphenoxy)-3-methylbutanamido]phenol (100 mg)
dioctyl phthalate (100 mg)
dicyclohexyl phthalate (100 mg)
gelatin (1200 mg)
5-chloro-2-(3,5-di-t-butyl-2-hydroxyphenyl)benzo-1,2,3-triazole (100 mg)
2-(3-dodecyl-2-hydroxy-5-methylphenyl)benzo-1,2,3-triazole (100 mg)
3,5-di-t-butyl-4-hydroxy(2,4-di-t-amylphenyl)benzoate (50 mg)
poly(N-t-butylacrylamide) (300 mg)
N,N-diethyl-2,4-di-t-amylphenoxyacetamide (100 mg)
2,5-di-t-octylhydroquinone (50 mg)
red-sensitive silver chlorobromide emulsion (200 mg)

The topmost layer is prepared with and without UV absorber;
with UV absorber:
2,5-di-t-octylhydroquinone (20 mg)
hexyl 5-[2,5-dihydroxy-4-(4-hexyloxycarbonyl-1,1-dimethylbutyl)phenyl]-5-methylhexanoate (20 mg)
gelatin (400 mg)
trinonyl phosphate (120 mg)
novel UV absorber Comp. No. 1 (385 mg)
without UV absorber:
gelatin (800 mg)

The hardener used is 2,4-dichloro-6-hydroxytriazine K salt solution, the wetting agent is the sodium salt of diisobutylnaphthalenesulfonic acid.

Three step wedges with a density difference of 0.3 log E per step are exposed onto each of the samples (with blue, green and red light, respectively). Then the processing process RA-4 (Kodak) for colour papers is carried out.

After exposure and processing, the reflectance densities in the red for the cyan step, in the green for the magenta step and in the blue for the yellow step are measured at a density of between 0.9 and 1.1 of the wedges. The wedges are then exposed in an Atlas exposure instrument at a total of 15 kJ/cm$^2$, and the reflectance densities are measured again.

In the case of the magenta wedge as well, the reflectance density before and after exposure is measured in the blue for the yellowing.

The presence of the UV absorbers reduces the dye density loss of the cyan, magenta and yellow image dye.

Example B7

Use in Cosmetics

A sun protection cream is prepared using the phases A, B and C described in the following tables:

| Phase A | |
|---|---|
| Ceteareth-6 (and) stearyl alcohol | 2% |
| Ceteareth-25 | 2% |
| Cetearyl alcohol | 5% |
| Caprylic/capric triglyceride | 5% |
| Cetearyl octanoate | 10% |
| Vaseline | 5% |
| Compound No. 11 | 4% |

| Phase B | |
|---|---|
| Propylene glycol | 3.0% |
| Carbopol 934 | 0.2% |
| H$_2$O | 63.53% |

| Phase C | |
|---|---|
| Triethanolamine | 0.27% |

The percentages indicated relate to the overall weight of the mixture comprising the phases A, B and C; the given names of the additives, where they are not chemical names, are CTFA designations (Cosmetic, Toiletry and Fragrance Association, USA).

Phases A and B are heated separately to 75–80° C. Then first phase B and subsequently phase C are added to phase A with homogenization. Subsequent homogenization is carried out.

An SPF analyser SPF® 290 (Manufacturer: Optometrix) is used to determine the light protection factor and UVA/UVB ratio of the resulting emulsion in accordance with the method of Diffey and Robson, J. Soc. Cosmet. Chem. 40, 127–133 (1989); the light protection factor is 6, the UVA/UVB ratio 0.87.

Use of compound No. 12 instead of compound No. 11 leads to a similar result.

Example B8

A sun protection cream is prepared using the phases A and B described in the following tables:

| Phase A | |
|---|---|
| Dimethicone | 2% |
| Isopropyl myristate | 9% |
| Stearyl alcohol | 10% |
| Stearic acid | 4% |
| Octyl methoxycinnamate | 4% |

-continued

| | |
|---|---|
| Compound No. 8 micronized, 250 nm | 3.2% |
| Phase B | |
| Triethanolamine | 1.2% |
| Carbomer 934 (1% strength) | 5.0% |
| H₂O | 61.6% |

The percentages indicated relate to the overall weight of the mixture comprising the phases A and B; the given names of the additives, where they are not chemical names, are CTFA designations (Cosmetic, Toiletry and Fragrance Association, USA).

Phase A is homogenized separately and very carefully and, like phase B, but separately, is heated to 75–80° C. Then phase B is added to phase A with vigorous stirring. The mixture is allowed to cool while stirring. The light protection factor of this suncream is 18 (determined as in Example B7).

Example B9
Action as UV Absorber in Photographic Layers

A gelatin layer is applied to a polyester base as described in Example B3. The maximum optical density ($OD_{max}$) of the UV filters prepared in this way is measured using a Lambda 15 spectrophotemeter from Perkin-Elmer; the results are given in the table below.

| Sample No. | Comp. of Formula 1 No. | $OD_{max}$ |
|---|---|---|
| a1 | 1 | 1.49 |
| a2 | 21 | 2.09 |
| a3 | 33 | 2.10 |
| a4 | 27 | 1.70 |
| a5 | 18 | 2.43 |
| a6 | 19 | 2.19 |
| a7 | 24 | 1.99 |
| a8 | 26 | 1.90 |
| a9 | 32 | 1.74 |
| a10 | 11 | 1.58 |
| a11 | 10 | 1.52 |
| a12 | 6 | 1.50 |

The novel compounds can be used to produce efficient UV filters for photographic layers.

Example B10

A polyethylene-coated base material is coated with chromogenic emulsions comprising the following components (amounts stated per m²):

| Sample | BI | BII |
|---|---|---|
| Gelatin | 5.10 g | 5.10 g |
| Hardener | 300 mg | 300 mg |
| Wetting agent | 85 mg | 85 mg |
| Silver bromide | 260 mg | 260 mg |
| Magenta coupler | M-9, 305 mg | M-2, 417 mg |
| Tricresyl phosphate | 305 mg | 208 mg |
| Stabilizer(s) | ST-11, 137 mg + ST-10, 91 mg | ST-2, 125 mg + ST-7, 83.4 mg |

The magenta couplers employed are of the formulae

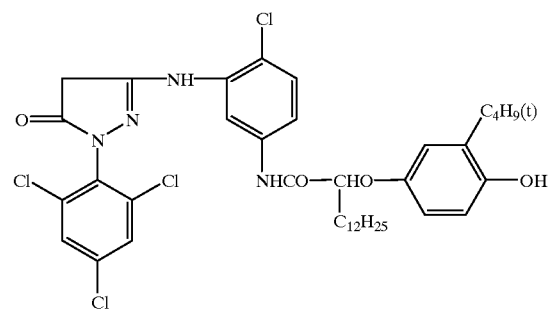

(M-2)

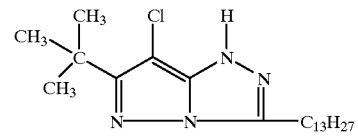

(M-9)

A step wedge with a density difference of 0.3 log E per step was exposed onto each of the resulting samples, which were then processed in the processing process P-94 of Agfa for negative colour papers.

To prepare the UV filter, a gelatin layer with the following composition is applied in the customary manner to a polyester base:

| Component | Amount (mg/m²) |
|---|---|
| Gelatin | 1200 |
| Tricresyl phosphate | 510 |
| Hardener | 40 |
| Wetting agent | 100 |
| Total amount of UVA | 300 |

The hardener is the potassium salt of 2-hydroxy-4,6-dichloro-1,3,5-triazine.

The wetting agent is sodium 4,8-diisobutyinaphthalene-2-sulfonate.

The gelatin layers are dried at 20° C. for 7 days.

The chromogenic layers are then exposed behind the UV filter layers b1 to b26, comprising novel UV absorbers (UVAs) and, in addition, one conventional UVA, in accordance with the table below, in an Atlas Ci35 Weather-o-meter® with a xenon lamp at 30 kJ/m². The reflectance density in the green region is measured before and after exposure.

| UVA | Ratio by mass | $\lambda_{max}$ | Density loss Layer B-I | Density loss Layer B-II |
|---|---|---|---|---|
| b1 | –/– | — | — | 84% | 90% |
| b2 | 21/HPT-30 | 70/30 | 349.0 | 44% | 46% |
| b3 | 21/HPT-30 | 80/20 | 348.7 | 43% | 47% |
| b4 | 21/HPT-30 | 90/10 | 346.3 | 37% | 47% |
| b5 | 8/HBT-8 | 50/50 | 350.4 | 39% | 44% |
| b6 | 8/HBT-8 | 80/20 | 348.1 | 39% | 44% |
| b7 | 21/HBT-8 | 80/20 | 347.1 | 40% | 48% |

-continued

| UVA | Ratio by mass | λmax | Density loss Layer B-I | Density loss Layer B-II |
|---|---|---|---|---|
| b8 | 21/HBT-8 | 90/10 | 346.3 | 39% | 47% |
| b9 | 1/HBT-4 | 80/20 | 347.9 | 43% | 45% |
| b10 | 21/HBT-4 | 50/50 | 347.9 | 42% | 46% |
| b11 | 21/HBT-4 | 80/20 | 346.4 | 46% | 47% |
| b12 | 21/HBT-4 | 90/10 | 346.1 | 42% | 46% |
| b13 | 33/HBT-4 | 90/10 | 347.9 | 40% | 47% |
| b14 | 33/HPT-53 | 70/30 | 348.8 | 37% | 49% |
| b15 | 33/HPT-53 | 90/10 | 346.1 | 43% | 48% |
| b16 | 33/HPT-54 | 70/30 | 350.0 | 40% | 44% |
| b17 | 33/HPT-54 | 80/20 | 348.9 | 50% | 40% |
| b18 | 33/HPT-54 | 90/10 | 347.8 | 47% | 58% |
| b19 | 27/HPT-54 | 90/10 | 345.2 | 42% | 43% |
| b20 | 21/HPT-51 | 70/30 | 349.8 | 38% | 38% |
| b21 | 21/HPT-51 | 80/20 | 347.9 | 37% | 37% |
| b22 | 21/HPT-52 | 90/10 | 346.7 | 36% | 45% |
| b23 | 33/HPT-51 | 90/10 | 348.1 | 39% | 58% |
| b24 | 33/HPT-51 | 70/30 | 349.3 | 38% | 50% |
| b25 | 33/HPT-52 | 90/10 | 346.6 | 39% | 58% |
| b26 | 33/HPT-52 | 70/30 | 346.1 | 42% | 50% |

The example shows that the novel compounds form efficient UV filters for protecting chromogenic layers.

Example B11

Gelatin layers are prepared as in Example B9. This time, the amount of UVA employed is chosen so as to give an optical density of 2 at $\lambda_{max}$. The samples are stored in a climatically controlled chamber for 21 days; then the loss in absorption which has occurred as a result of storage is measured. The results are shown in the table below; rH therein stands for relative atmospheric humidity.

| UV Absorber | Density loss after 21 days of storage at | |
|---|---|---|
| | 90° C., 50% rH | 80° C., 70% rH |
| 19 | 0% | 5% |
| 20 | 0% | 6% |
| 21 | 0% | 4% |
| 25 | 0% | 8% |
| 26 | 0% | 4% |
| 27 | 0% | 5% |

The results show that the novel compounds are outstandingly stable even under extreme climatic conditions.

What is claimed is:
1. A compound of the formula I

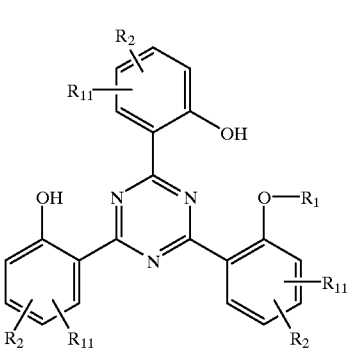

in which
$R_1$ is $C_1$–$C_{18}$alkyl; $C_5$–$C_{12}$cycloalkyl; $C_3$–$C_{18}$alkenyl; phenyl; $C_1$–$C_{18}$alkyl which is substituted by phenyl, OH, $C_1$–$C_{18}$alkoxy, $C_5$–$C_{12}$cycloalkoxy, $C_3$–$C_{18}$alkenyloxy, halogen, —COOH, —COOR$_4$, —O—CO—R$_5$, —O—CO—O—R$_6$, —CO—NH$_2$, —CO—NHR$_7$, —CO—N(R$_7$)(R$_8$), CN, NH$_2$, NHR$_7$, —N(R$_7$)(R$_8$), —NH—CO—R$_5$, phenoxy, $C_1$–$C_{18}$alkyl-substituted phenoxy, phenyl-$C_1$–$C_4$alkoxy, $C_6$–$C_{15}$bicycloalkoxy, $C_6$–$C_{15}$bicycloalkylalkoxy, $C_6$–$C_{15}$bicycloalkenylalkoxy, or $C_6$–$C_{15}$tricycloalkoxy; $C_5$–$C_{12}$cycloalkyl which is substituted by OH, $C_1$–$C_4$alkyl, $C_2$–$C_6$alkenyl or —O—CO—R$_5$; glycidyl;
—CO—R$_9$ or —SO$_2$—R$_{10}$; or R$_1$ is $C_3$–$C_{50}$alkyl which is interrupted by one or more oxygen atoms and/or substituted by OH, phenoxy or $C_7$–$C_{18}$alkylphenoxy;
or $R_1$ is one of the definitions —A; —CH$_2$—CH(XA)—CH$_2$—O—R$_{12}$; —CR$_{13}$R'$_{13}$—(CH$_2$)$_m$—X—A; —CH$_2$—CH(OA)—R$_{14}$; —CH$_2$—CH(OH)—CH$_2$—XA;

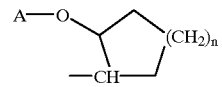

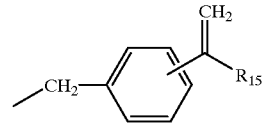

—CR$_{15}$R'$_{15}$—C(=CH$_2$)—R"$_{15}$; —CR$_{13}$R'$_{13}$—(CH$_2$)$_m$—CO—X—A;
—CR$_{13}$R'$_{13}$—(CH$_2$)$_m$—CO—O—CR$_{15}$R'$_{15}$—C(=CH$_2$)—R"$_{15}$ or —CO—O—CR$_{15}$R'$_{15}$—C(=CH$_2$)—R"$_{15}$, where A is —CO—CR$_{16}$=CH—R$_{17}$; the radicals
$R_2$, independently of one another, are $C_6$–$C_{18}$alkyl; $C_2$–$C_6$alkenyl; phenyl; $C_7$–$C_{11}$-phenylalkyl; COOR$_4$; CN; NH—CO—R$_5$; halogen; trifluoromethyl; —O—R$_3$;
$R_3$ embraces the definitions given for $R_1$;
$R_4$ is $C_1$–$C_{18}$alkyl; $C_3$–$C_{18}$alkenyl; phenyl; $C_7$–$C_{11}$phenylalkyl; $C_5$–$C_{12}$cycloalkyl; or is

83

$C_3$–$C_{50}$alkyl, which is interrupted by a spacer selected from —O—, —NH—, —NR$_7$—, —S—, and can be substituted by OH, phenoxy or $C_7$–$C_{18}$alkylphenoxy;

$R_5$ is H; $C_1$–$C_{18}$alkyl; $C_2$–$C_{18}$alkenyl; $C_5$–$C_{12}$cycloalkyl; phenyl; $C_7$–$C_{11}$phenylalkyl;

$C_6$–$C_{15}$bicycloalkyl; $C_6$–$C_{15}$bicycloalkenyl; $C_6$–$C_{15}$tricycloalkyl;

$R_6$ is H; $C_1$–$C_{18}$alkyl; $C_3$–$C_{18}$alkenyl; phenyl; $C_7$–$C_{11}$phenylalkyl; $C_5$–$C_{12}$cycloalkyl;

$R_7$ and $R_8$ independently of one another are $C_1$–$C_{12}$alkyl; $C_3$–$C_{12}$alkoxyalkyl;

$C_4$–$C_{16}$dialkylaminoalkyl; or are $C_5$–$C_{12}$cycloalkyl; or together are $C_3$–$C_9$alkylene, $C_3$–$C_9$oxaalkylene or $C_3$–$C_9$azaalkylene;

$R_9$ is $C_1$–$C_{18}$alkyl; $C_2$–$C_{18}$alkenyl; phenyl; $C_5$–$C_{12}$cycloalkyl; $C_7$–$C_{11}$phenylalkyl;

$C_6$–$C_{15}$bicycloalkyl, $C_6$–$C_{15}$bicycloalkylalkyl, $C_6$–$C_{15}$bicycloalkenyl, or $C_6$–$C_{15}$tricycloalkyl;

$R_{10}$ is $C_1$–$C_{12}$alkyl; phenyl; naphthyl or $C_7$–$C_{14}$alkylphenyl;

the radicals $R_{11}$ independently of one another are H; $C_1$–$C_{18}$alkyl; $C_3$–$C_6$alkenyl;

phenyl; $C_7$–$C_{11}$phenylalkyl; halogen; $C_1$–$C_{18}$alkoxy;

$R_{12}$ is $C_1$–$C_{18}$alkyl; $C_3$–$C_{18}$alkenyl; phenyl; phenyl which is substituted by one to three radicals $C_1$–$C_8$alkyl, $C_1$–$C_8$alkoxy, $C_3$–$C_8$alkenoxy, halogen or trifluoromethyl;

or is $C_7$–$C_{11}$phenylalkyl; $C_5$–$C_{12}$cycloalkyl; $C_6$–$C_{15}$tricycloalkyl; $C_6$–$C_{15}$bicycloalkyl;

$C_6$–$C_{15}$bicycloalkylalkyl; $C_6$–$C_{15}$bicycloalkenylalkyl; —CO—$R_5$; or is $C_3$–$C_{50}$alkyl which is interrupted by a spacing group selected from —O—, —NH—, —NR$_7$—, —S—, and can be substituted by OH, phenoxy or $C_7$–$C_{18}$alkylphenoxy;

$R_{13}$ and $R'_{13}$ independently of one another are H; $C_1$–$C_{18}$alkyl; phenyl;

$R_{14}$ is $C_1$–$C_{18}$alkyl; $C_3$–$C_{12}$alkoxyalkyl; phenyl; phenyl-$C_1$–$C_4$alkyl;

$R_{15}$, $R'_{15}$ and $R''_{15}$ independently of one another are H or $CH_3$;

$R_{16}$ is H; —$CH_2$—COO—$R_4$; $C_1$–$C_4$alkyl; or CN;

$R_{17}$ is H; —COO$R_4$; $C_1$–$C_{17}$alkyl; or phenyl;

X is —NH—; —NR$_7$—; —O—; —NH—$(CH_2)_p$—NH—; or —O—$(CH_2)_q$—NH—;

and the indices m is a number 0–19;

n is a number 1–8;

p is a number 0–4; and q is a number 2–4;

provided that at least one of the radicals $R_1$, $R_2$ and $R_{11}$ in formula I contains 2 or more carbon atoms.

2. A compound according to claim 1, in which $R_1$ is $C_1$–$C_{18}$alkyl; $C_5$–$C_{12}$cycloalkyl; $C_3$–$C_{12}$alkenyl; phenyl; $C_1$–$C_{18}$alkyl which is substituted by phenyl, OH, $C_1$–$C_{18}$alkoxy, $C_5$–$C_{12}$cycloalkoxy, $C_3$–$C_{18}$alkenyloxy, halogen, —COOH, —COO$R_4$, —O—CO—$R_5$, —O—CO—O—$R_6$, —CO—$NH_2$, —CO—NH$R_7$, —CO—N($R_7$)($R_8$), CN, $NH_2$, NH$R_7$, —N($R_7$)($R_8$), —NH—CO—$R_5$, phenoxy, $C_1$–$C_{18}$alkyl-substituted phenoxy, phenyl-$C_1$–$C_4$alkoxy, bornyloxy, norborn-2-yloxy, norbornyl-

84

2-methoxy, norborn-5-ene-2-methoxy, adamantyloxy; $C_5$–$C_{12}$cycloalkyl which is substituted by OH, $C_1$–$C_4$alkyl, $C_2$–$C_6$alkenyl and/or —O—CO—$R_5$; glycidyl; —CO—$R_9$ or —SO$_2$—$R_{10}$; or $R_1$ is $C_3$–$C_{50}$alkyl which is interrupted by oxygen and/or is substituted by OH, phenoxy or $C_7$–$C_{18}$alkylphenoxy;

or $R_1$ is —A; —$CH_2$—CH(XA)—$CH_2$—O—$R_{12}$; —$CR_{13}R'_{13}$—$(CH_2)_m$—X—A; —$CH_2$—CH(OA)—$R_{14}$; —$CH_2$—CH(OH)—$CH_2$—XA;

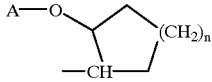

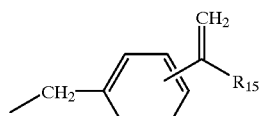

—$CR_{15}R'_{15}$—C(=$CH_2$)—$R''_{15}$; —$CR_{13}R'_{13}$—$(CH_2)_m$—CO—X—A;

—$CR_{13}R'_{13}$—$(CH_2)_m$—CO—O—$CR_{15}R'_{15}$—C(=$CH_2$)—$R''_{15}$ or —CO—O—$CR_{15}R'_{15}$—C(=$CH_2$)—$R''_{15}$, where A is —CO—$CR_{16}$=CH—$R_{17}$;

the radicals $R_2$ are $C_6$–$C_{18}$alkyl; $C_2$–$C_6$alkenyl; phenyl; —O—$R_3$ or —NH—CO—$R_5$ and the radicals $R_3$ independently of one another embrace the definitions given for $R_1$;

$R_4$ is $C_1$–$C_{18}$alkyl; $C_3$–$C_{18}$alkenyl; phenyl; $C_7$–$C_{11}$phenylalkyl; $C_5$–$C_{12}$cycloalkyl; or is $C_3$–$C_{50}$alkyl, which is interupted by a spacing group selected from —O—, —NH—, —NR$_7$—, —S—, and can be substituted by OH, phenoxy or $C_7$–$C_{18}$alkylphenoxy;

$R_5$ is H; $C_1$–$C_{18}$alkyl; $C_2$–$C_{18}$alkenyl; $C_5$–$C_{12}$cycloalkyl; phenyl; $C_7$–$C_{11}$phenylalkyl; norborn-2-yl; norborn-5-en-2-yl; adamantyl;

$R_6$ is H; $C_1$–$C_{18}$alkyl; $C_3$–$C_{18}$alkenyl; phenyl; $C_7$–$C_{11}$phenylalkyl; $C_5$–$C_{12}$cycloalkyl;

$R_7$ and $R_8$ independently of one another are $C_1$–$C_{12}$alkyl; $C_3$–$C_{12}$alkoxyalkyl;

$C_4$–$C_{16}$dialkylaminoalkyl; or are $C_5$–$C_{12}$cycloalkyl; or together are $C_3$–$C_9$alkylene, $C_3$–$C_9$oxaalkylene or $C_3$–$C_9$azaalkylene;

$R_9$ is $C_1$–$C_{18}$alkyl; $C_2$–$C_{18}$alkenyl; phenyl; $C_5$–$C_{12}$cycloalkyl; $C_7$–$C_{11}$phenylalkyl; norborn-2-yl; norborn-5-en-2-yl; adamantyl;

$R_{10}$ is $C_1$–$C_{12}$alkyl; phenyl; naphthyl or $C_7$–$C_{14}$alkylphenyl; the radicals $R_{11}$ independently of one another are H; $C_1$–$C_{18}$alkyl; or $C_7$–$C_{11}$phenylalkyl;

$R_{12}$ is $C_1$–$C_{18}$alkyl; $C_3$–$C_{18}$alkenyl; phenyl; phenyl which is substituted by one to three $C_1$–$C_8$alkyl, $C_1$–$C_8$alkoxy, $C_3$–$C_8$alkenoxy, halogen or trifluoromethyl; or is $C_7$–$C_{11}$phenylalkyl; $C_5$–$C_{12}$cycloalkyl; 1-adamantyl; 2-adamantyl; norbornyl;

norbornane-2-methyl-; —CO—$R_5$; or is $C_3$–$C_{50}$alkyl which is interrupted by a spacing group selected from —O—, —NH—, —NR$_7$—, —S— and can be substituted by OH, phenoxy or $C_7$–$C_{18}$alkylphenoxy;

$R_{13}$ and $R'_{13}$ independently of one another are H; $C_1$–$C_{18}$alkyl; phenyl;

$R_{14}$ is $C_1$–$C_{18}$alkyl; $C_3$–$C_{12}$alkoxyalkyl; phenyl; phenyl-$C_1$–$C_4$alkyl;

$R_{15}$, $R'_{15}$ and $R''_{15}$ independently of one another are H or $CH_3$;

$R_{16}$ is H; —$CH_2$—COO—$R_4$; $C_1$–$C_4$alkyl; or CN;

$R_{17}$ is H; —COO$R_4$; $C_1$–$C_{17}$alkyl; or phenyl;

X is —NH—; —N$R_7$—; —O—; —NH—$(CH_2)_p$—NH—; or —O—$(CH_2)_q$—NH—;

and the indices m is a number 0–19;

n is a number 1–8;

p is a number 0–4; and q is a number 2–4.

3. A compound according to claim 1 of the formula II

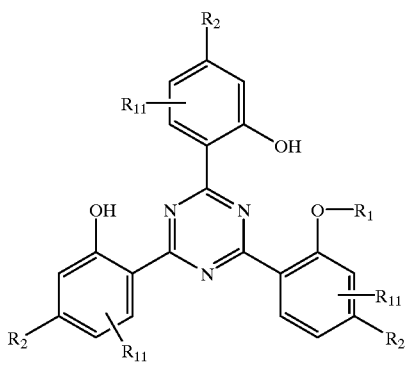

(II)

in which $R_1$, $R_2$ and $R_{11}$ are as defined for formula I.

4. A compound of the formula II according to claim 3, in which $R_1$ is $C_1$–$C_{18}$alkyl; $C_5$–$C_{12}$cycloalkyl; phenyl; $C_1$–$C_{18}$alkyl which is substituted by phenyl, OH, $C_1$–$C_{18}$alkoxy, $C_5$–$C_{12}$cycloalkoxy, —COOH, —COO$R_4$, —O—CO—$R_5$, phenyl-$C_1$–$C_4$alkoxy; or is cyclohexyl which is substituted by OH, $C_1$–$C_4$alkyl, $C_2$–$C_6$alkenyl and/or —O—CO—$R_5$;

or $R_1$ is one of the definitions —A; —$CH_2$—CH(XA)—$CH_2$—O—$R_{12}$; —$CR_{13}R'_{13}$—$(CH_2)_m$X—A; —$CH_2$—CH(OA)—$R_{14}$; —$CH_2$—CH(OH)—$CH_2$—XA;

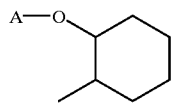

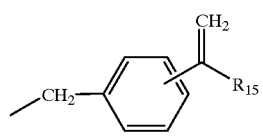

glycidyl; —$CR_{13}R'_{13}$—$(CH_2)_m$—C—O—$CR_{15}R'_{15}$—C(=$CH_2$)—$R''_{15}$ or —CO—O—$CR_{15}R'_{15}$—C(=$CH_2$)—$R''_{15}$, where A is —CO—$CR_{16}$=CH—$R'_{17}$; the radicals $R_2$ are —O—$R_3$ or —NH—CO—$R_5$ and the radicals $R_3$ independently of one another embrace the definitions given for $R_1$;

$R_4$ is $C_1$–$C_{18}$alkyl; $C_7$–$C_{11}$phenylalkyl; cyclohexyl; or $C_3$–$C_{50}$alkyl which is interrupted by —O— and can be substituted by OH, phenoxy or $C_7$–$C_{18}$alkylphenoxy;

$R_5$ is $C_1$–$C_{18}$alkyl; cyclohexyl; phenyl; $C_7$–$C_{11}$phenylalkyl;

$R_7$ is $C_1$–$C_{12}$alkyl or cyclohexyl;

$R_{11}$ is H; $R_{12}$ is $C_1$–$C_{18}$alkyl; phenyl; $C_1$–$C_8$alkyl- or $C_1$–$C_8$alkoxy-substituted phenyl; $C_7$—$C_{11}$phenylalkyl; $C_5$–$C_{12}$cycloalkyl; —CO—$R_5$; or is $C_3$–$C_{50}$alkyl which is interrupted by —O— and can be substituted by OH, phenoxy or $C_7$–$C_{18}$alkylphenoxy;

$R_{13}$ is H; $C_1$–$C_{18}$alkyl; phenyl;

$R'_{13}$ is H;

$R_{14}$ is $C_1$–$C_{18}$alkyl; phenyl; phenyl-$C_1$–$C_4$alkyl;

$R_{15}$, $R'_{15}$ and $R''_{15}$ independently of one another are H or $CH_3$;

$R_{16}$ is H; —$CH_2$—COO—$R_4$; $C_1$–$C_4$alkyl; or CN;

$R_{17}$ is H; —COO$R_4$; $C_1$–$C_{17}$alkyl; or phenyl;

X is —NH—; —N$R_7$—; or —O—;

and m is a number 0–19.

5. A compound of the formula II according to claim 3, in which $R_1$ is $C_1$–$C_{18}$alkyl; $C_5$–$C_{12}$cycloalkyl; $C_1$–$C_{18}$alkyl which is substituted by phenyl, OH, $C_1$–$C_{18}$alkoxy, —COO$R_4$, —O—CO—$R_5$; or cyclohexyl which is substituted by OH, $C_1$–$C_4$alkyl, $C_2$–$C_6$alkenyl;

or $R_1$ is one of the definitions —A; —$CH_2$—CH(XA)—$CH_2$—O—$R_{12}$; —$CR_{13}R'_{13}$—$(CH_2)_m$—X—A; —$CH_2$—CH(OA)—$R_{14}$; —$CH_2$—CH(OH)—$CH_2$—XA;

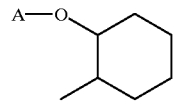

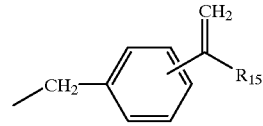

glycidyl; —$CR_{13}R'_{13}$—$(CH_2)_m$—CO—O—$CR_{15}R'_{15}$—C(=$CH_2$)—$R''_{15}$ or —CO—O—$CR_{15}R'_{15}$—C(=$CH_2$)—$R''_{15}$; where A is —CO—$CR_{16}$=CH—$R_{17}$; the radicals $R_2$ are —O—$R_3$ or —NH—CO—$R_5$ and the radicals $R_3$ independently of one another embrace the definitions given for $R_1$;

$R_4$ is $C_1$–$C_{18}$alkyl; $C_7$–$C_{11}$phenylalkyl or cyclohexyl;

$R_5$ is $C_1$–$C_{18}$alkyl;

$R_{11}$ is H;

$R_{12}$ is $C_1$–$C_{18}$alkyl; $C_7$–$C_{11}$phenylalkyl; $C_5$–$C_{12}$cycloalkyl; —CO—$R_5$;

$R_{13}$ is H or $C_1$–$C_{18}$alkyl;

$R'_{13}$ is H;

$R_{14}$ is $C_1$–$C_{18}$alkyl;

$R_{15}$, $R'_{15}$, $R''_{15}$, $R_{16}$ and $R_{17}$ independently of one another are H or $CH_3$;

X is —O—;

and m is a number 0–19.

6. A compound of the formula II according to claim 3, in which $R_2$ is —$OR_3$, $R_1$ and $R_3$ independently of one another are $C_1$–$C_{18}$alkyl; or are $C_2$–$C_6$alkyl which is substituted by OH, $C_1$–$C_{18}$alkoxy and/or —$COOR_4$; or are $CH_2COOR_4$; or are cyclohexyl which is unsubstituted or substituted by OH and/or $C_2$–$C_3$alkenyl; and $R_4$ is $C_1$–$C_6$alkyl; and $R_{11}$ is hydrogen.

7. 2,4,6-Tris(2'-hydroxy-4'-isopropyloxyphenyl)-1,3,5-triazine;

2,4,6-tris(2'-hydroxy-4'-n-hexyloxyphenyl)-1,3,5-triazine;

2,4,6-tris(2'-hydroxy-4'-n-heptyioxyphenyl)-1,3,5-triazine;

2,4,6-tris(2'-hydroxy-4'-ethoxycarbonylmethoxyphenyl)-1,3,5-triazine.

\* \* \* \* \*